(12) United States Patent
Sahney et al.

(10) Patent No.: US 11,801,143 B2
(45) Date of Patent: Oct. 31, 2023

(54) MULTI-LAYERED BIOMIMETIC OSTEOCHONDRAL IMPLANTS AND METHODS OF USING THEREOF

(71) Applicant: HYALEX ORTHOPAEDICS, INC., Lexington, MA (US)

(72) Inventors: Mira Sahney, Lexington, MA (US); David Myung, Lexington, MA (US); James Craig Fryman, Lexington, MA (US); Michael E. Hawkins, Lexington, MA (US)

(73) Assignee: HYALEX ORTHOPAEDICS, INC., Lexington, MA (US)

( * ) Notice: Subject to any disclaimer, the term of this patent is extended or adjusted under 35 U.S.C. 154(b) by 0 days.

(21) Appl. No.: 17/365,135

(22) Filed: Jul. 1, 2021

(65) Prior Publication Data
US 2023/0000628 A1    Jan. 5, 2023

(51) Int. Cl.
*A61F 2/30* (2006.01)
*A61F 2/28* (2006.01)

(52) U.S. Cl.
CPC ........ *A61F 2/30756* (2013.01); *A61F 2/2803* (2013.01); *A61F 2002/2825* (2013.01);
(Continued)

(58) Field of Classification Search
CPC .............. A61F 2/30756; A61F 2/2803; A61F 2002/2825; A61F 2002/2853;
(Continued)

(56) References Cited

U.S. PATENT DOCUMENTS 5,876,452 A * 3/1999 Athanasiou ......... A61F 2/30756
                                                        623/23.72
10,271,938 B2    4/2019 Altschuler
(Continued)

FOREIGN PATENT DOCUMENTS

EP    0650707 A1    5/1995
EP    1779875 A1    5/2007
(Continued)

OTHER PUBLICATIONS

International Search Report and Written Opinion for International Patent Application No. PCT/US2022/036016 dated Sep. 26, 2022, 18 pages.
(Continued)

*Primary Examiner* — Brian A Dukert
*Assistant Examiner* — Melissa A Hoban
(74) *Attorney, Agent, or Firm* — GOODWIN PROCTER LLP

(57) ABSTRACT

Provided herein are biomimetic osteochondral implants that are generally useful for the at least partial resurfacing of damaged cartilage within a joint. The implants are constructed to have a modular, layered structure in which the physical properties (e.g., stiffness and lubricity) or dimensions of each layer can be adjusted (e.g., by using the appropriate material and controlling the thickness thereof) based on the anatomy to be replaced. For example, the material and or thicknesses of the layers can be selected to approximate the physical properties and/or dimensions of cartilage (and, optionally, chondral and subchondral bone). Also provided herein are methods of treatment involving the use of said biomimetic osteochondral implants to repair an osteochondral defect in a joint.

30 Claims, 15 Drawing Sheets

(52) U.S. Cl.
CPC .............. A61F 2002/2853 (2013.01); A61F 2002/2871 (2013.01); A61F 2002/2892 (2013.01); A61F 2002/2896 (2013.01); A61F 2002/30757 (2013.01); A61F 2310/00023 (2013.01); A61F 2310/00071 (2013.01); A61F 2310/00089 (2013.01); A61F 2310/00179 (2013.01); A61F 2310/00592 (2013.01)

(58) Field of Classification Search
CPC ...... A61F 2002/2871; A61F 2002/2892; A61F 2002/2896; A61F 2002/30757; A61F 2310/00023; A61F 2310/00071; A61F 2310/00089; A61F 2310/00179; A61F 2310/00592

See application file for complete search history.

(56) References Cited

U.S. PATENT DOCUMENTS

| | | | |
|---|---|---|---|
| 2001/0004710 A1* | 6/2001 | Felt | C08L 75/04 623/17.12 |
| 2003/0055502 A1* | 3/2003 | Lang | G06F 30/00 623/16.11 |
| 2003/0077821 A1* | 4/2003 | Sah | A61L 27/3891 435/366 |
| 2003/0216669 A1* | 11/2003 | Lang | A61B 17/1675 600/587 |
| 2004/0133275 A1* | 7/2004 | Mansmann | A61F 2/30965 623/23.51 |
| 2004/0133276 A1* | 7/2004 | Lang | A61F 2/30756 623/14.12 |
| 2005/0043808 A1* | 2/2005 | Felt | C08G 18/4854 623/20.14 |
| 2005/0137713 A1* | 6/2005 | Bertram, III | A61F 2/38 623/23.44 |
| 2009/0088846 A1* | 4/2009 | Myung | A61L 27/34 623/14.12 |
| 2009/0240337 A1 | 9/2009 | Myung et al. | |
| 2010/0010114 A1* | 1/2010 | Myung | C08F 222/102 523/114 |
| 2010/0015202 A1 | 1/2010 | Semler et al. | |
| 2010/0032090 A1 | 2/2010 | Myung et al. | |
| 2011/0152868 A1 | 6/2011 | Kourtis et al. | |
| 2011/0177132 A1* | 7/2011 | Allon | A61P 19/00 435/395 |
| 2012/0209396 A1 | 8/2012 | Myung et al. | |
| 2012/0232657 A1 | 9/2012 | Myung et al. | |
| 2012/0277801 A1 | 11/2012 | Marik et al. | |
| 2013/0103157 A1 | 4/2013 | Kourtis et al. | |
| 2013/0131741 A1 | 5/2013 | Kourtis et al. | |
| 2013/0138210 A1 | 5/2013 | Myung et al. | |
| 2013/0138211 A1 | 5/2013 | Myung et al. | |
| 2013/0217829 A1 | 8/2013 | Myung et al. | |
| 2013/0261212 A1 | 10/2013 | Myung et al. | |
| 2017/0327624 A1 | 11/2017 | Kourtis et al. | |
| 2017/0348011 A1 | 12/2017 | Kourtis et al. | |
| 2018/0236136 A1 | 8/2018 | Kourtis et al. | |
| 2019/0224367 A1 | 7/2019 | Kourtis et al. | |

FOREIGN PATENT DOCUMENTS

| | | |
|---|---|---|
| EP | 2268331 A2 | 1/2011 |
| EP | 2626090 A2 | 8/2013 |
| GB | 2372707 A | 9/2002 |
| JP | H06287443 A | 10/1994 |
| JP | H06287443 A | 10/1994 |
| JP | P3176176 | 12/1994 |
| JP | 9-77809 | 3/1997 |
| JP | 10-500038 | 1/1998 |
| JP | 2002-514233 A | 5/2002 |
| JP | 2002-518564 A | 6/2002 |
| JP | 2002-518565 A | 6/2002 |
| JP | 2003-171475 A | 6/2003 |
| JP | 2004-512079 A | 4/2004 |
| JP | 2004-515311 A | 5/2004 |
| JP | 2005-305162 A | 11/2005 |
| JP | 2006-517842 A | 8/2006 |
| JP | 2007-501674 A | 2/2007 |
| WO | WO-94/01468 A1 | 1/1994 |
| WO | WO-95/30388 A1 | 11/1995 |
| WO | WO-98/06768 A1 | 2/1998 |
| WO | WO-99/45978 A1 | 9/1999 |
| WO | WO-99/67311 A1 | 12/1999 |
| WO | WO-99/67312 A1 | 12/1999 |
| WO | WO-0002937 A1 | 1/2000 |
| WO | WO-0043050 A1 | 7/2000 |
| WO | WO-0226848 A2 | 4/2002 |
| WO | WO-03009337 A2 | 1/2003 |
| WO | WO-2004/032767 A1 | 4/2004 |
| WO | WO-2004/055057 A1 | 7/2004 |
| WO | WO-2004/073563 A2 | 9/2004 |
| WO | WO-2004/091685 A2 | 10/2004 |
| WO | WO-2007/067697 A2 | 6/2007 |
| WO | WO-2007/068625 A1 | 6/2007 |
| WO | WO-2007/112305 A2 | 10/2007 |
| WO | WO-2008/100617 A1 | 8/2008 |
| WO | WO-2008/130604 A2 | 10/2008 |
| WO | WO-2009/071937 A1 | 6/2009 |
| WO | WO-2010/037685 A1 | 4/2010 |
| WO | WO-2010/059495 A2 | 5/2010 |
| WO | WO-2012/096997 A2 | 7/2012 |
| WO | WO-2015/023569 A1 | 2/2015 |
| WO | WO-2017/027590 A1 | 2/2017 |

OTHER PUBLICATIONS

U.S. Appl. No. 61/069,046, filed Mar. 12, 2008, Shalaby et al.
U.S. Appl. No. 61/229,735, filed Jul. 30, 2009, Forsell, Peter.
Balamurugan et al., "Development and Spectral Characterizaton of Poly(Methyl Methacrylate)/Hydroxyapalite Composite for Biomedical Applications," Trends Biomater. Artif. Organs, vol. 18(1): 41-45 (2004).
Barszczewska-Rybarek, Izabela M., "Quantitative Determination of Degree of Conversion in Photocured Poly(urethane-dimethacrylate)s by Fourier Transform Infrared Spectorscopy," Journal of Applied Polymer Science, vol. 123, 1604-1611 (2012).
Bobyn et al., The Optimum Pore Size for the Fixation of PoroSurfaced Metal Implants by the Ingrowth of Bone, Basic Science and Pathology, Section III, Clinical Orthopaedics and Related Research; vol. 150: 263-270 (1980).
Bone Cement Time Setting Chart (1 page).
Borden et al., "The sintered microsphere matrix for bone tissue engineering: In vitro osteoconductivity studies," Center for Advanced Biomaterials and Tissue Engineering: 421-429 (2001).
Brodbeck et al., "Biomaterial adherent macrophage apoptosis is increased by hydrophilic and anionic substrates in vivo," PNAS Early Edition 162124199, Applied Biological Sciences (6 pages) (2002).
Brown et al., "Solvent/Non-solvent Sintering: A Novel Route to Create Porous Microsphere Scaffolds for Tissue Regeneration," Journal of Biomedical Material Research Part B: Applied Biomaterials, 396-406 (2007).
Causton, B.E., Dental materials: 1981 Literature Review, Journal of Dentistry, vol. 12(1): 1-28 (1984).
Charley, John, "Anchorage of the Femoral Head Prosthesis to the Shaft of the Femur, The Journal of Bone and Joint Surgery," vol. 42 B(1): 28-30 (1960).
Chen and Baoquan, "Mechanical properties of polyepichlorohydrin polyurethane/poly(methyl methacrylate) IPNs," Chinese Journal of Applied Chemistry, vol. 12 (4): 5 pages (1995).
Christenson et al., "Antioxident inhibition of poly(carbonate urethane) in vivo biodegradtion," published Wiley InterScience: 480-490 (2005).
Covert et al., "Friction characteristics of a potential articular cartilage biomaterial," Science Direct, Wear, vol. 255 Case Study: 1064-1068 (2003).
Implant definition, Real Dictionary, www.realdictionary.com (2 pages). Dec. 1, 2013.

(56) References Cited

OTHER PUBLICATIONS

Dror et al., Gradient Interpenetrating Polymer Networks. I. Poly(ether Urethane) and Polyacrylamide IPN, Journal of Applied Polymer Science, vol. 26: 1741-1757 (1981).
Elbert, Donald L., "Liquid-liquid two phase systems for the production of porous hydrogels and hydrogel microspheres for biomedical applications: A tutorial review," Acta Biomater, vol. 7(1): 31-56 (2011).
Elmers Products, Inc., Material Safety Data Sheet, (www.elmers.com/msds/mp9420.htm), (7 pages) (2009).
Elsabee et al., "Gradient Interpenetrating Polymer Networks. II. Polyacrylamide Gradients in Poly(ether Urethane)," Journal of Applied Polymer Science, vol. 28: 2151-2166 (1983).
Esstech Inc., Urethane Dimethacrylate, Item # X-850-0000, www.esstechinc.com (1 page) (2015).
Evans et al., "The use of corneal organ culture in biocompatibility studies," Biomaterials, vol. 23: 1359-1367 (2002).
Frank, et al., POLY 270, "Structure-property relationships for hydrogels with applications to biomedical devices," 7th International Biorelated Polymers Symposium, (1 page) (Sep. 11, 2006).
Gao, et al., "Grafting of Hydrophilic Monomers Onto Polyurethane Membranes by Solution of Pre- absorbing Methods for Acceleration of Cell Compatibility," Chinese Journal of Polymer Science, vol. 19(5): 493-498 (2001).
Gong, et al., "Double-Network Hydrogels with Extremely High Mechanical Strength," Adv. Mater., vol. 15(14): 1155-1158 (2003).
Gorna and Gogolewski, "Biodegradable porous polyurethane scaffolds for tissue repair and regeneration," Journal of Biomedical Materials Research, Part A, pp. 128-138 (2005).
Gorna and Gogolewski, "Preparation, Degradation, and Calcification of Biodegradable Polyurethane Foams for Bone Graft Substitutes," Polymer Research, AO/ASIF Research Institute, pp. 814-827 (2002).
Goswami and Chakrabarty, "Engineering Properties of Novolac Resin-PMMA {Poly(methyl methacrylate)} IPN System," Engineering Properties of Novolac Resin-PMMA IPN System, Journal of Applied Polymer Science, vol. 93: 2764-2774 (2004).
Guelcher et al., "Synthesis of biocompatible segmented polyurethanes from aliphatic diisocyanates and diurea diol chain extenders," Science Direct, Acta Biomaterialia: 471-484 (2005).
Guelcher et al., Synthesis and In Vitro Biocompatibility of Injectable Polyurethane Foam Scaffolds, Tissue Engineering, vol. 12(5): 1247-1259 (2006).
Gunatillake et al., "Designing Biostable Polyurethane Elastomers for Biomedical Implants," Aust. J. Chem., vol. 56: 545-557 (2003).
Hern and Hubbell, "Incorporation of adhesion peptides into nonadhesive hydrogels useful for tissue resurfacing," Department of Chemical Engineering, University of Texas, pp. 266-276 (1997).
Hsieh et al., Compatibility and Morphology in Polyurethane and Polystyrene Ionomeric Interpenetrating Polymer Networks, Polymer Journal; vol. 21(1): 1-10 (1989).
International Search Report, PCT/US 08/01642, dated May 16, 2008, (1 page).
International Search Reort, PCT/US2016/046350, dated Oct. 14, 2016 (3 pages).
International Search Report, PCT/US2019/042193, dated Sep. 27, 2019 (3 pages).
Iwasaki et al., "Hydrogel-Like Elastic Membrane Consisting of Semi-Interpenetrating Polymer Networks Based on a Phosphorylcholine Polymer and a Segmented Polyurethane," Journal of Polymer Science, 68-78 (2002).
Joints of the Back, (www.ithaca.edu/faculty/lahr/LE2000/Back/Jointpage.htm, (3 pages) (2013).
Jones et al., "Sequential polyurethane-poly(methylmethacrylate) interpenetrating polymer networks as ureteral biomaterials: mechanical properties and comparative resistance to urinary encrustation," Journal of Materials Science: Material in Medicine 713-717 (1997).
Kagata et al., "Friction of Gels. 6. Effects of Sliding Velocity and Viscoelastic Responses of the Network," J. Phys. Chem B, vol. 106: 4596-4601 (2002).
Kaneko et al., "Mechanically Strong Hydrogels with Ultra-Low Frictional Coefficients," Adv. Mater., vol. 17(5): 535-538 (2005).
Kanie et al., Flexural properties of ethyl or methyl methacrylate-UDMA blend polymers, Dental Materials Journal, vol. 29(5): 575-581 (2010).
Khan et al., "Analysis and evaluation of a biomedical polycarbonate urethane tested in an in vitro study and an ovine arthroplasty model. Part I: materials selection and evaluation," Science Direct, Biomaterials, vol. 26: 621-631 (2005).
Kim et al., "Adhesion and growth of endothelial cell on amphiphilic PU/PS IPN surface: Effect of amphiphilic balance and immobilized collagen," Amphiphilic PU/PS IPN Surface, 613-621 (2002).
Kim, et al., "Electrical/pH Responsive Properties of Poly (2-acrylamido-2-methylpropane sulfonic acid)/Hyaluronic Acid Hydrogels," Journal of Applied Polymer Science, vol. 92(3): 1731-1736 (2004).
Kim et al., "Electrochemical Behavior of an Interpenetrating Polymer Network Hydrogel Composed of Poly(propylene glycol) and Poly(acrylic acid)," Journal of Applied Polymer Science, vol. 89: 2301-2305 (2003).
Kim et al., "Water sorption of poly(propylene glycol)/poly(acrylic acid) interpenetrating polymer network hydrogels," Science Direct, Reactive & Functional Polymers. vol. 55: 69-73 (2003).
Kwong and Power, "A comparison of the shrinkage of commerical bone cements when mixed under vacuum," The Journal of Bone and Joint Surgery, vol. 88-B(1): 120-122 (2005).
Lam and Gupta, "Update on Ureteral Stents," Urology, vol. 64(1): 9-15 (2004).
Lamba et al., "Polyurethanes in Biomedical Applications, The Chemistry of Polyurethane Copolymers," (13 pages) (1998).
Lee et al., "Interpenetrating polymer network hydrogels based on poly(ethylene glycol) macromer and chitosan," Carbohydrate Polymers, vol. 41: 197-205 (2000).
Lewis, Gladius, "Properties of Acrylic Bone Cement: State of the Art Review," Acrylic Bone Cement Properties, 155-182 (1996).
Lipatov and Karabanova, "Gradient interpenetrating polymer networks," Journal of Materials Science, vol. 30:1095-1104 (1995).
Lu and Anseth," Release Behavior of High Molecular Weight Solutes from Poly(ethylene glycol)-Based Degradable Networks," Macromolecules, vol. 33: 2509-2515 (2000).
Maroudas, "Permeability of Articular Cartilage," Nature, vol. 219 (1968): 1260-1261 (2 pages).
Matinlinna et al., "Isocyanato- and Methacryloxysilanes Promote Bis-GMA Adhesion to Titanium," Journal of Dental Research, vol. 84(4): 360-364 (2005).
MIT_edu, Internet Archive, Waybackmachine, http://web.mit.edu/course/3/3.11/www/modules/props.pdf (2 pages) (2013).
Morgan and Keaveny, "Dependence of yield strain of human trabecular bone on anatomic site," Journal of Biomechanics, vol. 34: 569-577 (2001).
Mow and Huiskes, "Friction, Lubrication, and Wear of Articular Cartilage and Diarthrodial Joints," Basic Othopaedic Biomechanics and Mechano-Biology, Third Edition: 459-461 (2005).
Myung et al., "Biomimetic strain hardening in interpenetrating polymer network hydrogels," Science Direct, Polymer vol. 48: 5376-5387 (2007).
Myung, David, "Structure, Properties and Medical Device Applications of Mechanically Enhanced, Biomimetic Hydrogel Alloys," A dissertation submited to the Department of Chemical Engineerging of Stanford University (210 pages) (2007).
Nanci et al., "Chemical modification of titanium surfaces for covalent attachment of biological molecules," Protein Coupling to Titanium, Journal of Biomedical Material Research, pp. 324-335 (1996).
Material Safety Data Sheet, Product Name: New Fast Cure-Dries White Gorilla Glue (4 pages) (2007).
Material Safety Data Sheet, Product Name: New Stronger-Faster Gorilla Glue (4 pages) (2007).
Ohman et al., "Mechanical testing of cancellous bone from the femoral head: Experimental errors due to off-axis measurements," Journal of Biomechanics, vol. 40: 2426-2433 (2007).
Orr et al., Shrinkage stresses in bone cement, Science Direct, Biomaterials, vol. 24: 2933-2940 (2003).

(56) References Cited

OTHER PUBLICATIONS

Pan et al., "A study on the friction properties of poly(vinyl alcohol) hydrogel as articular cartilage against titanium alloy," Science Direct, Wear. Vol. 262: 1021-1025 (2007).
Park and Nho, Synthesis of PVA/PVP hydrogels having two-layer by radiation and their physical properties, Science Direct, Radiation Physics and Chemistry, vol. 67: 361-365 (2003).
Polyurethane Insulation, Thermal conductivity—temperature and k-values, The Engineering Toolbox, www.Engineergtoolbox.com (3 pages) (2011).
Puska et al., "Exothermal Characteristics and Release of Residual Monomers from Fiber-reinforced Oligomer-modified Acrylic Bone Cement," Journal of Biomaterials Applications, vol. 20: 51-64 (2005).
Revzin et al., "Fabrication of Poly(ethylene glycol) Hydrogel Microstructures Using Photolithography," Langmuir, vol. 17: 5440-5447 (2001).
Saito et al., "Preparation and Properties of Transparent Cellulose Hydrogels," Journal of Applied Polymer Science, vol. 90: 3020-3025 (2003).
Scholes et al., "Compliant layer acetabular cups: friction testing of a range of materials and designs for a new generation of prosthesis that mimics the natural joint, Proc. ImechE, vol. 220 (Part H): Journal Engineering in Medicine" pp. 583-596 (2006).
Product Specification: Product Name: Methyl methacrylate M55909; Sigma-Aldrich Product (1 page).
Simon et al., "Study of Two Grafting Methods for Obtaining a 3-Aminopropyltriethoxysilane Monolayer on Silica Surface," Journal of Colloid and Interface Science, vol. 251: 278-283 (2002).
Simplex P Bone Cement, Products, Stryker, Orthopaedics, (16 pages) (2006).
Spector et al., "Porous Polymers for Biological Fixation," Clinical Orthopaedics and Related Research, No. 235: 207-219 (1998).
Spinal Anatomy the Regions of the Spine, Laser Spine Institute (5 pages) (Dec. 2, 2013). (http://www.neurosurgical.com/neuro_medical_info/spinal_anatomy.htm).
Stammen et al., "Mechanical properties of a novel PVA hydrogel in shear and unconfined compression," Biomaterials. vol. 22: 799-806 (2001).
Swieszkowski et al., "An elastic material for cartilage replacement in an arthritic shoulder joint," Biomaterials, vol. 27: 1534-1542 (2006).
Tanaka et al., "Polymer Properties on Resins composed of UDMA and Methacrylates with the Carboxyl Group," Dental Materials Journal, vol. 20(3): 206-215 (2001).
Tariq et al., "Sodium benzoate attenuates iminodipropionitrile-induced behavioral syndrome in rats," Behay Pharmacol., vol. 15(8): 585-588 (2004).
Tawfik, Dan S., "Amidation of Carboxyl Groups," The Protein Procols Handbook, Edition No. 2: 477-478 (2002).
Thermal Conductivity of some common Material and Gases, The Engineering Toolbox, www.engineeringtoolbox.com/thermal-conductivity-d_429.html (2 pages) Oct. 21, 2011.
Van Landuyl et al., "Reinforcement of osteosynthesis screws with brushite cement," Bone, vol. 25(2), Supplement 1: 95S-98S, 11 pages (1999).
Wittemann et al., "Adsorption of proteins on spherical polyelectrolyte brushes in aqueous solution," Phys. Chem. Chem. Phys., vol. 5: 1671-1677 (2003).
Wright et al., "Wear studies on prosthetic materials using the pin-on-disc machine," Biomaterials, vol. 3, 8 pages (1982).
Written Opinion PCT/US2008/001642 dated May 16, 2008 (5 pages).
Written Opinion PCT/US2016/046350 dated Oct. 14, 2016 (8 pages).
Written Opinion PCT/US2019/042193, dated Sep. 27, 2019 (6 pages).
Written Opinion PCT/US2008/004976 dated Oct. 17, 2009 (6 pages).
Xiao et al., "Covalent Attachment of Cell-Adhesive, (Arg-Gly-Asp)-Containing Peptides to Titanium Surfaces," Langmuir, vol. 14: 5507-5516 (1998).
Yang, et al., "Preparation of poly(acrylic acid) modified polyurethane membrane for biomaterial by UV radiation without degassing," AA/PU Membranes by UV Without Degassing, pp. 133-139 (1997).
Yim et al., "Biocompatibility of poly(ethylene glycol)/poly(acrylic acid) interpenetrating polymer network hydrogel particles in RAW 264.7 macrophage and MG-63 osteoblast cell lines," Journal Production, 9 pages (2008).
Zhu et al., "Promoting the cytocompatibility of polyurethane scaffolds via surface photo-grafting polymerization of acrylamide," J. Mater Sci Mater Med, vol. 15(3): 283-289 (2004).

\* cited by examiner

MULTI-LAYERED BIOMIMETIC OSTEOCHONDRAL IMPLANTS AND METHODS OF USING THEREOF

BACKGROUND

Many different injuries or constant stress can wear down articular cartilage, the gliding surfaces of a joint. Cartilage lesions, particularly in weight-bearing joints, often fail to heal on their own and can be associated with pain, loss of joint function, and long-term complications such as osteoarthritis. In the United States, 1.2 million patients per year are diagnosed with a knee cartilage lesion, while only 550,000 patients per year receive knee cartilage repair surgery. Still, there is a significant satisfaction gap of patients diagnosed with cartilage injury, who decline current surgical standard-of-care due to poor outcomes and long rehabilitation—more than 30% of micro-fracture surgeries fail. Furthermore, osteochondral injuries are considered by some to be not just naturally but also therapeutically irreversible with current treatment parameters. Inferior repair commonly occurs, with stable regeneration of hyaline cartilage being a rare outcome. Accordingly, unmet needs in cartilage lesion repair include improved joint function and pain-reduction, higher effectiveness of intervention, faster return to weight-bearing and normal activities, shorter rehabilitation time, long-term implant effectiveness, applicability to a wide range of patients and variety of lesions, repair by a single surgery, and rapid surgeon adoption of an effective technique.

Some tissue regeneration techniques for cartilage defects range from simple micro-fracture techniques (drilling a multitude of holes through the cartilage defect into subchondral bone) to multistep cartilage transplantation procedures. Regenerative approaches have several shortcomings. For example, they require a long recovery period before allowing the patient to return to full weight-bearing and activity levels, results are highly variable based on individual patient factors such as age and body-mass-index, and they are generally unsuitable for middle-aged or older patients due to poor ability to regenerate hyaline cartilage, often resulting in production of fibro-cartilage having inferior properties. Furthermore, regenerative approaches have not demonstrated any viable method for successful interfacing or anchoring of regenerated cartilage with bone. Many attempts have been made at chondral regeneration and repair or osteo regeneration and repair but have not addressed the osteochondral complex which is relevant to positive clinical outcomes. Additionally, even for those patients with initial benefits, long term results are often elusive. Availability of tissue supply, high costs and the need for multiple surgical procedures are all additional challenges for regenerative approaches. The shortcomings of tissue regeneration techniques have prompted investigations into the use of synthetic implants.

While synthetic materials such as metals and most polymers are generally more durable than the cartilage, they fail to mimic the properties of the native tissue closely enough, and tend to adversely influence the health of the surrounding tissue and damage the opposing cartilage surface under articulation, thereby limiting the lifetime of such implants and hastening failure of the opposing cartilage surface. Other materials fail because they have tear strength that is too low and weak mechanical properties, as compared with cartilage, and often are unable to be properly fixed to the patient's bone in a way that can provide a stable long-term solution. Accordingly, there is a need for new osteochondral implants with improved properties and techniques of repairing focal cartilage defects.

SUMMARY

Methods of repairing articular cartilage defects and osteochondral mimetic implants and systems suitable for use in the methods are disclosed herein. Provided herein are biomimetic osteochondral implants that are multilayered constructs that, through the thickness thereof, mimic the properties (e.g., stiffness) of articular cartilage and, in some implementations, the underlying subchondral bone. The underlying multilayer structure is achieved by multiple zones that are attached together by mechanical connection, chemical bonding, biological adhesion, and/or other attachment mechanisms. Mimicking properties of the cartilage or other tissue to be replaced, as closely as possible, provides benefits such as improved stress transfer from the articulating surface to subchondral bone and, in the case of one-sided repair of a joint, the preservation of the cartilage counterface. The disclosure relates, in part, to the observation that tissues respond to applied loads and the resultant stresses by remodeling. If an osteochondral implant is formed from materials having mechanical properties that differ greatly from the mechanical properties of the surrounding tissue, the shape and/or amount of tissue surrounding an implantation site may change, thereby compromising the long-term success of the implant. Accordingly, it is an advantage of this disclosure to provide an osteochondral implant that provides properties similar to the surrounding native cartilage and bone, such that the implant better responds to physiological loads without compromising the health of the native cartilage and bone. In illustrative examples, the implant includes three zones, with an articulating zone, a base zone, and a middle zone, the middle zone having a first surface that attaches to the underside of the articulating zone, a second surface that attaches to the base zone, and a thickness and stiffness between the first and second surfaces that enables the middle zone to absorb part of the articulation load. In some implementations, the middle zone mimics the middle zone of natural cartilage in stiffness, but is hydrophobic and stronger than fibro-cartilage.

In a first aspect, provided herein is a biomimetic osteochondral implant. The implant has a bearing zone, a base zone configured to be attached to bone (e.g., subchondral bone, cancellous bone, sclerotic bone) upon implantation of the implant, and a hydrophobic middle zone positioned between the bearing zone and the base zone. The bearing zone comprises a compliant surface configured for articulation within a diarthrodial or other joint, an under surface, a first thickness extending between the compliant surface and the under surface, and a first compressive modulus with a first stiffness. The middle zone has a shaped first surface, a second surface, and a second thickness extending therebetween, the shaped first surface comprising a perimeter and an external face spaced within the perimeter and attached to the under surface of the bearing zone, wherein the under surface of the bearing zone conforms in shape to the face, and the middle zone further has a second compressive modulus with a second stiffness, the second stiffness being greater than the first stiffness. The base zone has an outer base surface attached to the second surface of the middle zone, an inner base surface configured to attach to bone, and a third thickness extending between the inner base surface and outer base surface, and having a third compressive modulus with a third stiffness, the third stiffness being greater than the second stiffness.

In some implementations, the bearing zone comprises a biphasic polymer. The biphasic polymer may have a water composition of at least 10%, at least 20%, at least 30%, at least 40%, or more. In some implementations, the biphasic polymer has a water composition gradient between the compliant surface and the under surface. For example, the water composition gradient has a water composition of less than 10%, less than 5%, or less than 1% at the under surface. For example, the water composition gradient has a water composition of more than 30%, more than 40%, more than 50%, about 40%, about 45%, or about 50% at the compliant surface. For example, the water gradient provides a composition of about 5% water at the under surface and 40% to 50% water at the compliant surface. In some implementations, the compliant surface is lubricious. In some implementations, the under surface is non-lubricious. In some implementations, the bearing zone comprises urethane. In some implementations, the bearing zone includes a water-swellable interpenetrating polymer network (IPN) or semi-IPN, the base zone includes a porous metal, and the middle zone includes a copolymer comprising a urethane dimethacrylate monomer and a monomer selected from methyl methacrylate, acrylamide, and diamethylacrylamide.

In some implementations, a contact interface formed between the face and the under surface and extending across at least 50% of the face. For example, the contact interface extends across at least 50%, at least 75%, at least 85%, or at least 95% of the face.

In some implementations, the implant has at least one post structure in the bearing zone, middle zone or base zone. The at least one post structure may have a plurality of posts in the middle zone. For example, the at least one post structure is positioned at the shaped first surface or at the second surface.

In some implementations, the implant comprises a central axis extending through the bearing zone, middle zone and base zone, each having an axis and being aligned coaxially along the central axis. In some implementations, the second thickness is variable with a first height extending between the second surface and the first surface at a first position along the first surface, and a second height extending between the second surface and the first surface at a second position along the first surface. For example, the first height has a maximum at a position along the perimeter and the second height has a maximum at a position within the face. The second height may be aligned co-axially with the axis of the base zone. In some implementations, the middle zone is plano-convex or plano-concave. In some implementations, the implant has a tapered region extending along the face from the maximum second height toward the perimeter. In some implementations, the first height maximum is higher than the second height maximum. For example, the tapered region forms a concave curve. In some implementations, the first height maximum is lower than the second height maximum. For example, the tapered region forms a convex curve.

In some implementations, the perimeter includes a curved edge extending circumferentially about the central axis. In some implementations, a ridge region extends radially across the face. In some implementations, a plurality of ridges protrude into the under surface. In some implementations, the face includes multiple regions with differing respective radii of curvature.

In some implementations, the second thickness at a position along the perimeter has a boundary height of 0.01 mm to 10 mm, 0.2 mm to 5 mm, or about 1 mm. The second thickness of the middle zone may taper toward the perimeter such that the boundary height is less than 0.1 mm. In some implementations, the bearing zone and middle zone extend axially from the outer base surface to the compliant surface over an axial length of 2 mm to 10 mm or 4 mm to 4.5 mm. In some implementations, the perimeter encompasses an area having a width of 5 mm to 15 mm (where the area is circular, the width is the diameter of the circle). In some implementations, the first thickness is 1 mm to 5 mm.

In some implementations, the second stiffness is 50 MPa to 500 MPa. In some implementations, the first stiffness is 40 MPa to 150 MPa, and the third stiffness is 1.5 GPa to 11 GPa. In some implementations, the bearing zone has a stiffness gradient extending from the under surface to the compliant surface of greater than or equal to 1 kPa/mm. In some implementations, the middle zone is configured to deform between 1% to 20% under physiologic load (e.g., about 3 MPa stress), with repeatable recovery of greater than or equal to 70% of the deformation when the physiological load is removed. In some implementations, the bearing zone has the ability to deform between 1% to 40% under physiological load with repeatable recovery of >70% of the deformation when said load is removed. In some implementations, when the bearing layer and middle layer are attached, the implant has the ability to deform between 5% to 20% under physiological loads, with repeatable recovery of greater than or equal to 80% or greater than or equal to 95%.

In some implementations, the base zone comprises at least one of a porous metal, a polymer, a ceramic, bone, or synthetic bone. For example, the porous metal comprises one or more of titanium, tantalum, stainless steel, cobalt chrome, a nickel-titanium alloy, or a zirconium alloy; and wherein the polymer comprises one or more of a porous polymer, polyetheretherketone (PEEK), polyethylene, polysulfone, a poly ester, a polyether imide polypropylene, or any other suitable engineering polymer or porous polymer.

In some implementations, the inner base surface is configured to be attached to a distal femur. In some implementations, the inner base surface is configured to be attached to a proximal tibia region. The implant may be adapted to repair or replace cartilage or cartilage and bone in a diarthrodial or other joint in the body, such as a knee joint (e.g., a condyle, a patellofemoral joint, a total knee joint, a meniscus, a patella, or a tibial plateau), ankle joint (e.g., talar or tibial surfaces), an elbow joint (e.g., proximal ulna, distal humerus, or radial head), a shoulder joint (e.g., a labrum, a glenoid, a humeral head or any portion thereof), a hand joint (e.g., a metacarpal joint, a finger joint, a thumb joint, or a base of thumb joint), a hip joint (e.g., the acetabular surface, a femoral head or a portion of either surface), a foot joint (e.g., a metatarsal joint or a toe joint), a jaw joint (e.g., a temporomandibular joint), a wrist joint, and a vertebral joint (e.g., an intervertebral facet joint). In some implementations, the bearing and middle zones are deployed on the outer base surface, and the base zone is metal or polymer and configured with a pre-formed attachment mechanism (e.g., a screw, post, digitation, or other component) on one end (e.g., the distal or proximal femur) that can attach mechanically to the bone, for example by screwing, posting, interdigitation or otherwise. In other applications, the implant is deployed by integration into an existing joint replacement component, for example a metal or polymer femoral head in a hip repair. In such cases, the existing metal or polymer implant (e.g., the femoral head), already attached to the bone (e.g., the proximal femur) in a previous surgery, serves as the base zone, and an implant having preformed bearing and middle zones (as disclosed herein) is attached directly to that existing metal or polymer base zone.

In another aspect, provided herein is a method for repairing a cartilage lesion on an articulating surface within an orthopedic joint (e.g., a diarthrodial joint) comprising subchondral or other bone. The lesion is at least partially surrounded by exterior cartilage on the articulating surface, and a portion of the exterior cartilage provides a region with a native tissue line for articulation. The method comprising the steps of (i) preparing a surgical site in the exterior cartilage region by removing at least a portion of the cartilage surrounding the lesion and leaving a hole that extends through the exterior cartilage region and into the bone, wherein the hole in the exterior cartilage has an inside diameter; (ii) providing an biomimetic osteochondral implant comprising a bearing zone and a base construct, the bearing zone having an under surface and a compliant surface with an outer face and a first perimeter having an outside diameter, the compliant surface configured to change shape upon articulation within the joint so the outer face conforms in shape to an opposing surface of the orthopedic joint; (iii) passing the implant into the hole and into bone so that the base construct interfaces directly with the bone; and (iv) anchoring the implant to the bone so that the outer face of the compliant surface is offset in height relative to the native tissue line of the exterior cartilage. It should be understood that the implant may be anchored such that the offset is zero at one or more locations along the compliant surface. The implant may be the implant according to any of the implementations of the first or second aspects.

In some implementations, the bearing zone comprises a biphasic polymer. The biphasic polymer may have a water composition of at least 10%, at least 20%, at least 30% or more. In some implementations, the biphasic polymer has a water composition gradient between the compliant surface and the under surface. The composition gradient is configured so that the composition of water changes along the thickness of the biphasic polymer, from its compliant external surface at one end to its internal under surface, with a bulk region in between, so as to provide a proper connection to the hydrophobic middle layer and the hydrophilic articulating surface. The gradient includes a water composition at the compliant surface, a water composition at the under surface, and a bulk water composition extending between the compliant surface and the under surface. In some implementations, the water composition is highest at the compliant surface and lowest at the under surface (e.g., near 0), forming an essentially hydrophobic interface with the middle layer of the construct, with the bulk water composition being at a level in between that of the two surfaces. The water composition at the compliant surface can be adjusted as needed in combination with adjustment of the rest of the gradient. In some implementations, the water composition at the compliant surface is at least 25%, and may be higher, while the water composition at the under surface is low (e.g., less than 10%, less than 5%, or less than 1% (or even approach 0 or is 0)). The bulk water composition is distributed at an operating condition that provides an optimal aqueous balance and transition between the hydrophilic compliant surface and the hydrophobic under surface. In implementations, the bulk water composition is in the 25%-41% range (e.g., 27-34%) and may be distributed as a gradient between that range, so as to provide a smooth transition between the compliant surface and the under surface, or may be distributed at a generally constant level at a point within the range (e.g., 27, or 34%). In some implementations, the compliant surface is lubricious. In some implementations, the under surface is non-lubricious. In some implementations, the bearing zone comprises polyurethane. In some implementations, the implant is plano-convex (flat on one side and convex on the other) or plano-concave (flat on one side and concave on the other). In some implementations, the base construct comprises a porous metal. In some implementations, the bearing zone comprises a stiffness gradient between the compliant surface and the under surface. For example, the stiffness gradient comprises a stiffness at the compliant surface that is less than a stiffness at the under surface, where stiffness varies between the compliant surface and the under surface.

In some implementations, the bearing zone is a first polymeric layer disposed between the compliant surface and the under surface, and wherein the base construct comprises a porous layer configured to attach directly to the bone and second polymeric layer attached to the first polymeric layer at a middle interface between the under surface and a shaped surface of the second polymeric layer, such that the second layer is disposed between the middle interface and the porous layer. In some implementations, the first polymeric layer has a first stiffness and the second polymeric layer has a second stiffness, and wherein the second stiffness is greater than the first stiffness. The porous layer may have a third stiffness greater than the second stiffness. In some implementations, the second polymeric layer comprises a copolymer of urethane dimethacrylate monomer comprising a hard segment and a soft segment, and methyl methacrylate monomer. For example, the hard segment of the urethane dimethacrylate of the first polymeric adhesive is formed from one or more of 1,5-naphthalene diisocyanate (NDI), 2,6 toluene diisocyanate or 2,4 toluene diisocyanate (TDI), 3,3-bitoluene diisocyanate (TODI), cyclohexyl diisocyanate (CHDI), hexamethyl diisocyanate (HDI), isophorone diisocyanate (IPDI), methylene bis(p-phenyl) isocyanate, methylene diphenylisocyanate (MDI), and methylene bis(p-cyclohexyl) isocyanate (HMDI). For example, the soft segment of the urethane dimethacrylate monomer is formed from one or more of polybutadiene, polyethylene oxide (PEO), hydroxy terminated butadiene, hydroxybutyl-terminated polydimethylsiloxane (PDMS), hydroxyl terminated polyisobutylene, poly(1,6-hexyl-1,2-ethyl carbonate), polycaprolactone, polycarbonate, polyethylene adipate, polyhexamethylene carbonate glycol, polypropylene oxide (PPO), polytetramethylene adipate, poly(dimethylsiloxane), and poly(tetramethylene oxide) (PTMO). In some implementations, the first polymeric layer is a water-swellable interpenetrating polymer network (IPN) or semi-IPN that comprises a first polymeric network comprising the thermoplastic polymer and a second polymeric network.

In some implementations, the surgical site is at the distal femur, the proximal tibia, the patella, the distal tibia, distal fibula, calcaneus, talus, the tibiofibular joint, the proximal humerus, the glenoid, the proximal femur, the pelvis, the distal humerus, the proximal ulna, the proximal radius, the distal radius, the distal ulna, the carpals, the distal metacarpal, the proximal phalanx, the metatarsal, or other joint surfaces having articular cartilage. In some implementations, the lesion is partially or fully surrounded by tissue.

In some implementations, step (i) comprises using at least one of an awl, a surgical drill, a burr, a reamer, an alignment guide, a pin, an incisor, a cutter, or a wire. Step (i) may comprise inserting a wire or a pin into the lesion via a guide; placing a drill, a burr, or a reamer over the wire or pin; and forming the hole using the drill, burr, or reamer. In some implementations, step (i) is performed with a single instrument, such as a self-guided surgical drill having a reamer function, so that instrument changes during the procedure are minimized. In some implementations, step (i) comprises resurfacing of the bone within the hole. In some implementations, the method further comprises, before step (iii), checking a depth of the hole. For example, checking the depth comprises inserting a trial implant into the hole, the trial implant mimicking the implant. In some implementations, step (iii) comprises using an implant inserting device which releasably holds the implant. In some implementations, step (iv) comprises using a mallet and a tamp to fully seat the implant within the hole. In some implementations, one or more of steps (i)-(iv) are performed through an arthroscope. In some implementations, the method further comprises closing the surgical site.

The hole may be shaped such that the implant has a press-fit in the hole when anchored. In some implementations, at least part of the compliant surface is offset from the native tissue line in a direction distal to the bone. In some implementations, at least part of the compliant surface is offset from the native tissue line in a direction proximal to the bone. In some implementations, the bearing zone is aligned laterally along the first perimeter with the exterior cartilage, such that the bearing zone is in contact with the exterior cartilage.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIG. 4B illustrates the idealized curvature of implant after loading where the conformity of the implant to the native joint surface has been improved and now closely approximates the original joint line (dotted line);

FIG. 5A illustrates the biomimetic osteochondral implant post-implantation but before being subjected to physiological load, in which the outer edge of the compliant surface is situated at or offset from the cartilage surface while the center of the implant is thicker, causing a mismatch in the conformity with the opposing side of the joint. FIG. 4B illustrates the idealized curvature of the implant after loading where the implant surface conforms to the original joint line, thereby allowing the implant to closely articulate with the opposing joint surface;

FIG. 6A illustrates an implant with a circular compliant surface modeled into a representative convex joint surface; FIG. 6B illustrates an implant with an elongated oval compliant surface modeled into a representative convex joint surface;

DETAILED DESCRIPTION

Figure 1A:
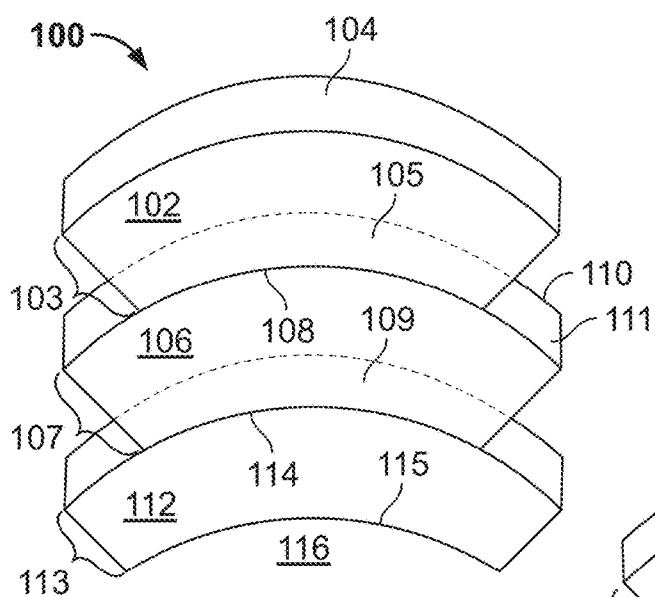
FIG. 1A depicts a vertical cross-section of a three-layered biomimetic osteochondral implant, according to an illustrative implementation.

To provide an overall understanding of the systems, method, and devices described herein, certain illustrative embodiments will be described. Although the embodiments and features described herein are specifically described for use in connection with cartilage lesion repair, it will be understood that all the components and other features outlined below may be combined with one another in any suitable manner and may be adapted and applied to other types of medical therapy, patient health, and material construction.

Certain terms are used herein to describe various aspects of the disclosure. Some definitions are provided for ease of reference, and others are provided by the use of terms in context throughout the application. It should be understood that the scope of terms includes any species known to those skilled in the art, whether specifically recited or not.

As used herein, "carboxylic acid groups" may refer to both non-ionized (protonated) and ionized (carboxylate) forms of these groups. For purposes of this application, "sulfonic acid groups" may refer to both non-ionized (protonated) and ionized (sulfonate) forms of these groups.

As used herein, an "interpenetrating polymer network" or "IPN" is a material comprising two or more polymer networks which are at least partially interlaced on a molecular scale, but not covalently bonded to each other, and cannot be separated unless chemical bonds are broken. A "semi-interpenetrating polymer network" or "semi-IPN" is a material comprising one or more polymer networks and one or more linear or branched polymers characterized by the penetration on a molecular scale of at least one of the networks by at least some of the linear or branched macromolecules. Semi-interpenetrating polymer networks are distinguished from interpenetrating polymer networks because the constituent linear or branched polymers can, in principle, be separated from the constituent polymer network(s) without breaking chemical bonds; they are polymer blends.

A "polymer" is a substance with repeating single species units, including homopolymers (a polymer derived from one species of monomer) and copolymers (a polymer derived from more than one species of monomer). A "hydrophobic polymer" may be a pre-formed polymer network having at least one of the following two properties: (1) a surface water contact angle of at least 45° and (2) exhibits water absorption of 2.5% or less after 24 hours at room temperature according to ASTM test standard D570. A "hydrophilic polymer" may be a polymer network having a surface water contact angle less than 45° and exhibits water absorption of more than 2.5% after 24 hours at room temperature according to ASTM test standard D570. An "ionic polymer" is as a polymer comprised of macromolecules containing ionic monomers (e.g., monomers with carboxylate group, sulfonate groups, or both), ionizable monomers (e.g., monomers with protonated carboxyl groups, protonated sulfonate groups, or both), or both ionic monomers and ionizable monomers, typically, at least 2% by weight ionic or ionizable monomers (or both), irrespective of their nature and location. A "thermoplastic polymer" is one which melts or flows when heated and can be re-melted repeatedly to form other shapes or products, unlike thermoset polymers which can only be heated and formed once. Thermoplastic polymers may be covalently (chemically) crosslinked. "Phase separation" is defined as the conversion of a single-phase system into a multi-phase system; for example, the separation of two immiscible blocks of a block co-polymer into two phases, with the possibility of a small interphase in which a small degree of mixing occurs.

"About" can be understood to mean plus or minus 20% of a value. For example, "about 20 mm" covers a range of 16 mm to 24 mm.

Aspects of the disclosure include the biomimetic osteochondral implants, kits or systems comprising the implants and one or more tools for implanting the implants, and methods for manufacturing and implanting the implants.

Biomimetic Osteochondral Implant

Provided herein are biomimetic osteochondral implant that are generally useful for the replacement of damaged cartilage and the partial or complete resurfacing of cartilage within a joint. The implants are constructed to have a modular, layered structure in which the physical properties (e.g., stiffness and lubricity) and dimensions of each layer can be adjusted (e.g., by using the appropriate material and controlling the thickness and stiffness thereof) based on the anatomy to be replaced. For example, the material and or thicknesses of the layers can be selected to approximate the physical properties, function and dimensions of cartilage (and, optionally, chondral and subchondral bone), such that the implant is cartilage mimetic. Also provided herein are methods of treatment involving the use of biomimetic osteochondral implants to repair an osteochondral defect in a joint.

The biomimetic osteochondral implants of the present disclosure can be made in a variety of shapes and sizes, depending on the specific joint in which the implant is to be deployed. The implant may be adapted to repair or replace cartilage or cartilage and bone in a joint in the body, such as a knee joint (e.g., a condyle, a patellofemoral joint, a total knee joint, a meniscus, a patella, or a tibial plateau), ankle joint (e.g., talar or tibial surfaces), an elbow joint (e.g., proximal ulna, distal humerus, or radial head), a shoulder joint (e.g., a labrum, a glenoid, a humeral head or any portion thereof), a hand joint (e.g., a metacarpal joint, a finger joint, a thumb joint, or a base of thumb joint), a hip joint (e.g., the acetabular surface, a femoral head or a portion of either surface), a foot joint (e.g., a metatarsal joint or a toe joint), a jaw joint (e.g., a temporomandibular joint), a wrist joint, and a vertebral joint (e.g., an intervertebral facet joint). In some applications, the implant may be deployed by integration with an existing joint replacement component, for example a metal or polymer femoral head that may have been placed in a previous hip repair. In such cases, the existing metal or polymer implant (e.g., the femoral head which is itself joined to a femoral stem), already attached to the bone (e.g., the proximal femur) in the previous surgery, serves as the base zone, and an implant having bearing and middle zones (as disclosed herein) is attached directly to that existing metal or polymer base zone. In some implementations, the base zone is configured as a metal or polymer with a pre-formed attachment mechanism (e.g., a screw, post, digitation, or other component) on one end (e.g., the distal or proximal femur) and configured to attach mechanically to the bone, for example by screwing, posting, interdigitation or otherwise. Plasma coating or other porous layer may also be applied to one or more surfaces of the base zone and middle zone. The base zone can accordingly be configured as a ball, disc, cylinder, or other shape appropriate to provide suitable anchoring force to the base, e.g., as a triangle, quadrilateral. While examples provided herein describe use of the implant in repair of a diarthrodial joint, it should be understood that the implant may also be used for repair of other tissues and joints, including but not limited to the spine, the meniscus, and other bone or cartilage structures. The implant may articulate against native tissue or against another implant (e.g., an implant according to the present disclosure, a ceramic implant, a metal (e.g., CoCr) implant, or a polymer implant (e.g., PEEK or ultra high molecular weight polyethylene (UHMWPE) implant). For example, a joint injury may be repaired by implanting two biomimetic osteochondral implants on the opposing surfaces of the joint. The entirety of one or both of the opposing surfaces may be replaced.

Figure 6A:
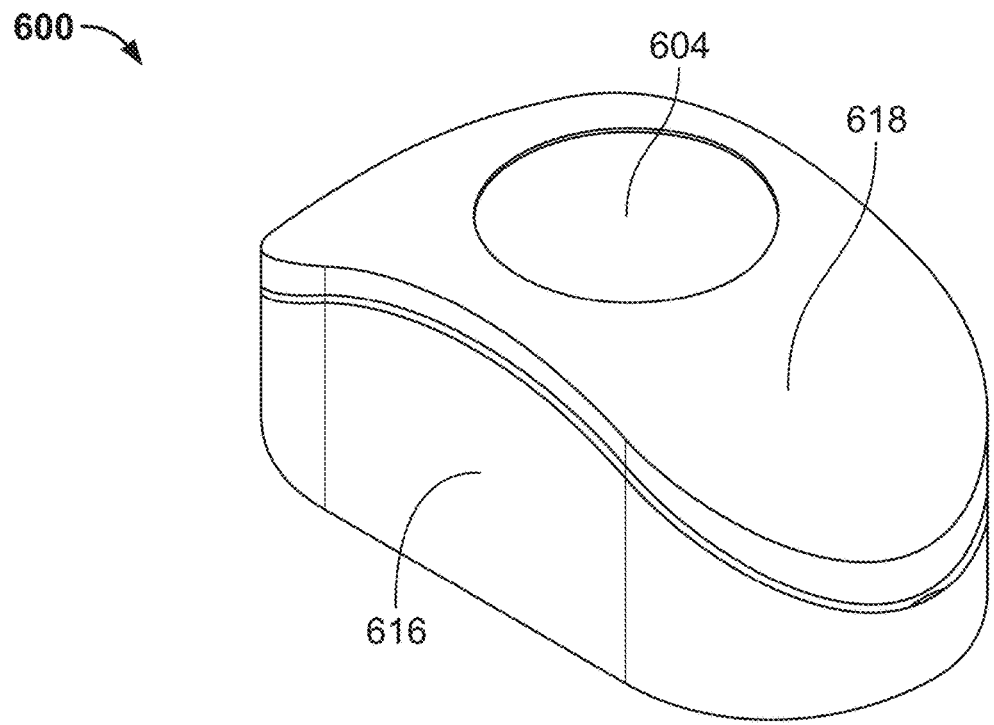
FIGS. 6A and 6B depict biomimetic osteochondral implants, according to illustrative implementations, that are inserted into surgical sites.
Figure 6B:
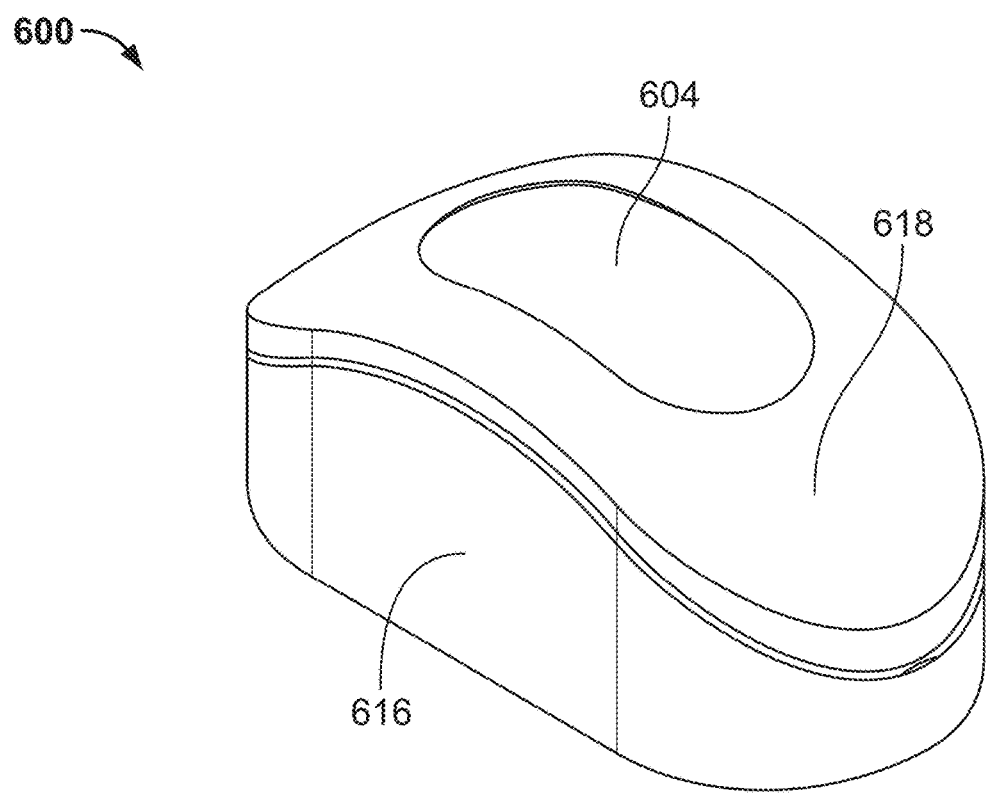

In some implementations, the biomimetic osteochondral implant, or a portion thereof (e.g., the lubricious top surface; FIG. 6A), defines a circular profile. In some embodiments, the biomimetic osteochondral implant, or a portion thereof (e.g., the lubricious top surface; FIG. 6B), for example, defines an elongated oval profile. Other non-limiting examples of shapes that the biomimetic osteochondral implant (or a portion thereof) may take are shown in FIGS. 7A-7D and 9A-9J.

In some implementations, the biomimetic osteochondral implant is shaped as a plug (e.g., a cylindrical plug) for partial resurfacing of joint surfaces. In some implementations, the biomimetic osteochondral implant includes a stem portion formed on or attached to the bone-contacting surface (i.e., the bottom surface a base) of the implant adapted for insertion into a hole or opening in a bone. The stem may be press fit into a hole or opening in the bone, leaving the lubricious top surface of the implant to be exposed to act as prosthetic cartilage.

In some implementations, the biomimetic osteochondral implant is axisymmetric or symmetric along one or more vertical planes. For example, it can be cylindrical with a dome shape on its outer surface with a single radius of curvature. Alternatively, it can have two or more radii of curvature. For example, the implant has a radius of curvature in one plane and a larger radius of curvature in a perpendicular plan, thus making it more "sloped" in one direction and less sloped in the perpendicular plane. In a natural joint surface such as the condyle of the knee, there may be two major curvature planes, one that runs along the flexion/extension axis of the knee (referred to herein as "the major radius"), and the other that is perpendicular to this plane, which has a smaller radius of curvature ("the minor radius"). There may also be more than two radii of curvature. These radii of curvature may also vary depending on the exact location on the joint surface. For example, an implant may be placed within an osteochondral defect that approximates the curvature(s) of the surrounding joint surface. Over time within the joint, the compliant surface reshapes under physiologic loads, such that the lubricious top surface takes on the radius or radii of curvature of the surrounding joint surface (FIGS. 4A, 4B, 5A, and 5B). The biomimetic osteochondral implants of the present disclosure can adapt to any joint geometries, including substantially convex joint surfaces, substantially concave joint surfaces, substantially flat joint surfaces, or joint surfaces that have both convex and concave curvatures. Thus, the implant can, e.g., start convex and become more convex, flat, or concave depending on the shape of the surrounding joint surface; start flat and become concave or convex; or start concave and become even more concave (more steeply curved).

In some implementations, an axisymmetric implant having a single radius of curvature is inserted into an implantation site in which the natural cartilage has a radius of curvature that differs from that of the implant. Post-implantation, a compliant surface of the implant reshapes under physiologic loads, and the radius of curvature of the implant substantially matches the radius of curvature of the natural cartilage, which results in a smooth continuity of curvature for the repaired joint on and around the implant.

In some implementations, an axisymmetric implant having a single radius of curvature is inserted into an implantation site in which the natural cartilage has two radii of curvature that differ from that of the implant. Post-implantation, the compliant surface of the implant reshapes under physiologic loads and defines two radii of curvature that match the radii of curvature of the natural cartilage, which results in a smooth continuity of curvature for the repaired joint on and around the implant.

In some implementations, an implant having two different (e.g., perpendicular) radii of curvature is inserted into an implantation site in which the natural cartilage has two radii of curvature that differ from those of the implant. Post-implantation, the compliant surface of the implant reshapes under physiologic loads and defines two radii of curvature that match the radii of curvature of the natural cartilage, which results in a smooth continuity of curvature for the repaired joint on and around the implant.

Figure 1B:
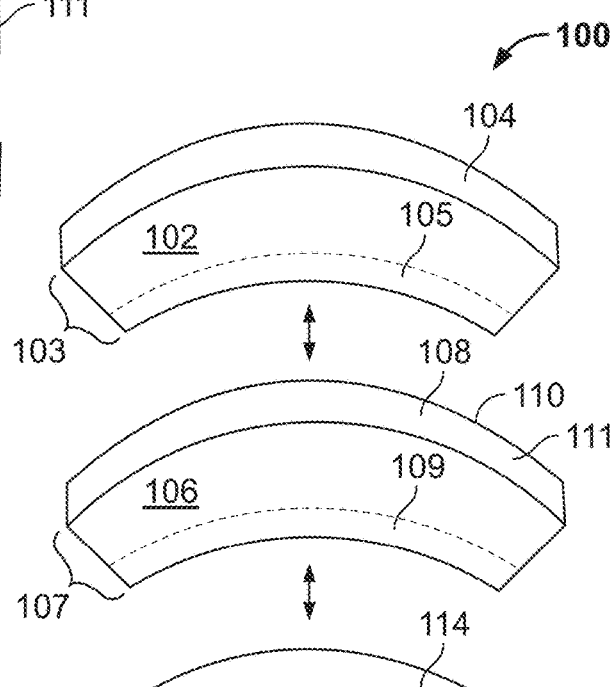
FIG. 1B depicts an exploded view of the cross-section of FIG. 1A.

FIG. 1A shows a vertical cross-section of a three-layered biomimetic osteochondral implant 100 according to an illustrative example. The implant 100 includes a bearing zone 102, a middle zone 106, and a base zone 112. Bearing zone 102 has a compliant surface 104, an under surface 105 opposite compliant surface 104, a first thickness 103 extending between compliant surface 104 and under surface 105, and a first compressive modulus with a first stiffness. Middle zone 106 has a shaped first surface 108, a second surface 109 opposite first surface 108, a second thickness 107 extending between first surface 108 and second surface 109, and a second compressive modulus with a second stiffness greater than the first stiffness. The shaped first surface comprises a perimeter 110 and an external face 111 spaced within perimeter 110. External face 111 and under surface 105 are attached (e.g., mechanically connected, chemically bonded, biologically affixed, or otherwise attached). As illustrated, the under surface 105 conforms in shape to face 111. Base zone 112 has an outer base surface 114 attached to second surface 109, an inner base surface 115 opposite outer base surface 114 and configured to attach to bone 116, a third thickness 113 extending between outer base surface 114 and inner base surface 115, and a third compressive modulus with a third stiffness greater than the second stiffness. FIG. 1B shows an exploded view of the layers of implant 100. While the surfaces in implant 100 are shown as having convex shapes, where the given shape curves or bulges outwards, it should be understood that any of the surfaces may be flat, concave (as shown where the shape bulges inward, in the alternative form of implant 100 in FIG. 1C), or any combination of flat, convex, or concave surface regions. It is understood that any convex and concave surfaces, such as those depicted in FIGS. 1A and 1B or elsewhere herein, may be asymmetric or symmetric.

Various materials may be used to construct each of the layers of implant 100. Suitable materials include polymers, ceramics, metals, synthetic bone, regenerated tissue, and other suitable materials. Suitable materials for bearing zone 102 in particular may include materials that have lubricious properties. For example, bearing zone 102 is constructed from a material that provides a lubricious compliant surface 104 and a non-lubricious under surface 105.

In some implementations, one of the layers, such as bearing zone 102, comprises a biphasic polymer including a polymer and water. For example, the biphasic polymer may have a water composition of at least 10%, at least 20%, at least 30%, at least 40%, at least 50%, or at least 60%. The biphasic polymer may have a water composition that is distributed consistently throughout the bearing zone 102, or the water may be distributed in a gradient extending within the bearing zone, for example from one surface to an opposite surface, or extending only partially within the bearing zone. The water composition gradient is configured so that the composition of water changes along the thickness of the zone, from its compliant external surface at one end to its internal under surface, with a bulk region in between, so as to provide a proper connection to the hydrophobic middle layer and the hydrophilic articulating surface. More particularly, the gradient includes a first water composition at the compliant surface, a second water composition at the under surface, and a bulk water composition extending between those two surfaces. In some implementations, for example those useful for repairing diarthrodial joints, the water is distributed in the bearing zone so the water composition is highest at the compliant surface and lowest at the under surface (e.g., at or near 0), to provide an essentially hydrophobic, non-lubricious interface with the middle layer of the construct, with the bulk water being distributed at a composition in between the respective water compositions of the two surfaces. That arrangement provides a lubricious interface for joint articulation, on one side, and a hydrophobic, non-lubricious connection surface to the middle layer on the other side of the bearing zone. The water composition at the compliant surface can be adjusted as needed in combination with adjustment of the rest of the gradient. For example, the water gradient may extend between compliant surface 104 and under surface 105. The water gradient may range from less than 1% at one part in the biphasic polymer to at least 20%, or at least 30%, or at least 40% at another part in the biphasic polymer, for example the gradient may have a water composition of less than 1% at a hydrophobic side (e.g., at under surface 105 which, in a distal femoral implant, may be at a position just proximal of the interface with the middle zone), and at least 20%, at least 30%, at least 40%, or at least 50% at an opposite, more hydrophilic side (e.g., at compliant surface 104, which in the distal femoral implant is the articulating surface of the bearing zone). In some implementations, the water composition at the compliant surface is at least 25%, and may be higher (e.g., 40-50%, e.g., 40%, 45% or 50%, or even 60% to 80%), providing the lubricious quality; while the water composition at the under surface is low (e.g., less than 10%, less than 5%, or less than 1% (or even approach 0 or is 0)), providing the non-lubricious quality. In the bulk region, the bulk water composition is distributed at an operating condition that provides an optimal aqueous balance and transition between the hydrophilic compliant surface and the hydrophobic under surface. In implementations, the bulk water composition is in the 25%-41% range (e.g., 27-34%) and may be distributed as a gradient between that range, so as to provide a smooth transition between the compliant surface and the under surface, or may be distributed at a generally constant level between the two surfaces, for example at a point within the range (e.g., 27, or 34%).

The biphasic polymer may be a water-swellable interpenetrating polymer network (IPN) or semi-IPN that comprises a first polymeric network comprising the thermoplastic polymer and a second polymeric network comprising a polymer having carboxylic acid groups or derivatives thereof, wherein the IPN or semi-IPN has a concentration of the carboxylic acid groups or derivatives thereof that is at maximum at the compliant surface 104 and decreases to zero or substantially zero within a bulk of the IPN or semi-IPN. The carboxylic acid groups or derivatives thereof may include underivatized carboxylic acid groups, sulfonic-acid-derivatized carboxylic acid groups, or a mixture thereof. For example, the polymer having carboxylic acid groups or derivatives thereof is formed from one or more monomers selected from acrylic acid, methacrylic acid, crotonic acid, linolenic acid, maleic acid, fumaric acid, and derivatives thereof. The carboxylic acid groups may be completely underivatized or may include sulfonic-acid derivatized carboxylic acid groups (a mixture of underivatized and derivatized groups, or the groups are completely derivatized). The sulfonic-acid derivatized carboxylic acid groups maybe taurine-derivatized carboxylic acid groups. In some implementations, the thermoplastic polymer is not water-based but functionally conformable to the joint geometry and sufficiently biocompatible so as to be used instead of biphasic polymer, for example polyurethane, e.g., polyether urethane or other forms of polyurethane, in the bearing zone of a construct.

In some implementations, a layer, such as middle zone 106, comprises urethane or a urethane-based material. In some implementations, the urethane-based material is a copolymer of urethane dimethacrylate monomer comprising a hard segment and a soft segment, and methyl methacrylate monomer. For example, middle zone 106 may be formed from a copolymer of about 60% (w/w) to about 99% (w/w) (e.g., about 60% (w/w) to about 80% (w/w)) urethane dimethacrylate monomer, and about 1% (w/w) to about 40% (w/w) (20% (w/w) to about 40% (w/w)) methyl methacrylate monomer. In some implementations, the hard segment of the urethane dimethacrylate of the first polymeric adhesive is formed from one or more of 1,5-naphthalene diisocyanate (NDI), 2,6 toluene diisocyanate or 2,4 toluene diisocyanate (TDI), 3,3-bitoluene diisocyanate (TODI), cyclohexyl diisocyanate (CHDI), hexamethyl diisocyanate (HDI), isophorone diisocyanate (IPDI), methylene bis(p-phenyl) isocyanate, methylene diphenylisocyanate (MDI), and methylene bis(p-cyclohexyl isocyanate) (HMDI). In some implementations, the soft segment of the urethane dimethacrylate monomer is formed from one or more of polybutadiene, polyethylene oxide (PEO), hydroxy terminated butadiene, hydroxybutyl-terminated polydimethylsiloxane (PDMS), hydroxyl terminated polyisobutylene, poly (1,6-hexyl-1,2-ethyl carbonate), polycaprolactone, polycarbonate, polyethylene adipate, polyhexamethylene carbonate glycol, polypropylene oxide (PPO), polytetramethylene adipate, poly(dimethylsiloxane), and poly(tetramethylene oxide) (PTMO). For example, the hard segment of the urethane dimethacrylate monomer may be formed from MDI and the soft segment of the urethane dimethacrylate may be formed from PTMO. In some implementations, the soft segment of the urethane dimethacrylate of the polymeric adhesive layer may be formed from a mixture of PTMO having different molecular weights, e.g., molecular weights ranging from about 500 Da to about 1250 Da.

In some implementations, a layer of implant 100, such as base zone 112, comprises a metal (e.g., titanium, tantalum, stainless steel, cobalt chrome, nickel-titanium, zirconium, or alloys thereof), a polymer (e.g., PEEK, PE, PS, or PP), a ceramic, bone, or synthetic bone. Base zone 112 may be attached to bone 116 via mechanical or physical means (such as those of FIGS. 8A-8H) immediately upon implantation. At some period after implantation, new bone may have grown into base zone 112 from bone 116, anchoring implant 100 in place.

Figure 1C:
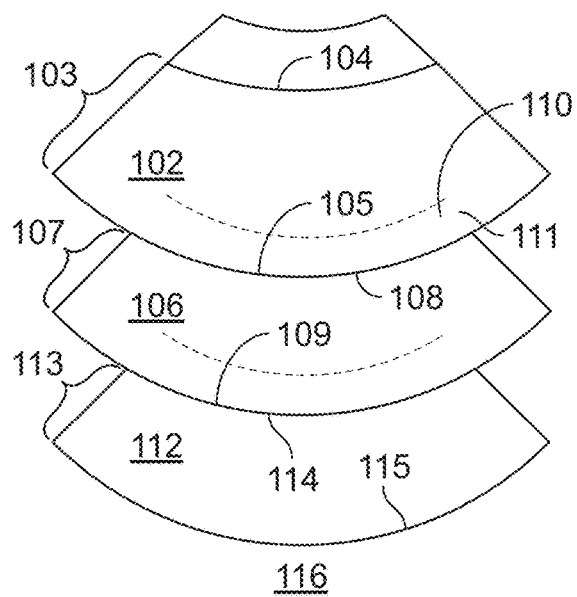
FIG. 1C depicts a vertical cross-section of a three-layered biomimetic osteochondral implant, according to an alternative illustrative implementation.

External face 111 of shaped first surface 108 has a shape (i.e., a topography or surface contour), and under surface 105 conforms to that shape of external face 111. The conforming shape of under surface 105 may then be translated through bearing zone 102 to a conforming shape of compliant surface 104, such that compliant surface 104 also reflects the shape of external face 111. Accordingly, external face 111 may be shaped in a particular manner (e.g., convex as shown in FIGS. 1A and 1B, concave as shown in FIG. 1C, or any of the shapes shown in FIGS. 14A-14J) in order to give compliant surface 104 a shape that approximates a native cartilage surface shape of a site where implant 100 is inserted. The shape of compliant surface 104 may be offset from the surrounding native cartilage surface at the site, such that physiological loading applied to implant 100 via compliant surface 104 causes compliant surface 104 to approximate the native cartilage surface shape. In some implementations, a contact interface is formed between external face 111 and under surface 105. The contact interface may extend across at least 50%, at least 75%, at least 90%, at least 95%, or 100% of external face 111 or under surface 105.

Various attachment mechanisms (e.g., mechanical, chemical, or biological) may be used to attach each of bearing zone 102, middle zone 106, and base zone 112 to each other or to surrounding native cartilage or bone (e.g., bone 116 below base zone 112). Any of the attachment mechanisms described in relation to and shown in FIGS. 8A-8H may be used in implant 100. Suitable attachments include a post structure (e.g., a singular post or plurality of posts in middle zone 106 at shaped first surface 108 or second surface 109, spikes, hooks, screws, adhesive, chemical bonds, sutures, barbs, plugs, or other forms of interdigitation or mechanisms known to those skilled in the art. Attachment mechanisms may be integrally formed in any of the zones of implant 100 or may comprise separate material.

Any of first thickness 103, second thickness 107, or third thickness 113 may have a height of 1 mm to 10 mm, 1 mm to 9 mm, 1 mm to 8 mm, 1 mm to 7 mm, 1 mm to 6 mm, 1 mm to 5 mm, 1 mm to 4 mm, 1 mm to 3 mm, 1 mm to 2 mm, about 1 mm, about 2 mm, about 3 mm, about 4 mm, about 5 mm, about 6 mm, about 7 mm, about 8 mm, about 9 mm, or about 10 mm.

Implant 100 and each layer may have a specified geometry. For example, the geometry of implant 100 or a zone may be created during manufacturing or may result from conformation to a geometry of a neighboring zone or native tissue/bone. In some implementations, implant 100 comprises a central axis extending through bearing zone 102, middle zone 106, and base zone 112, each of which having an axis and being aligned coaxially along the central axis.

Figure 3B:
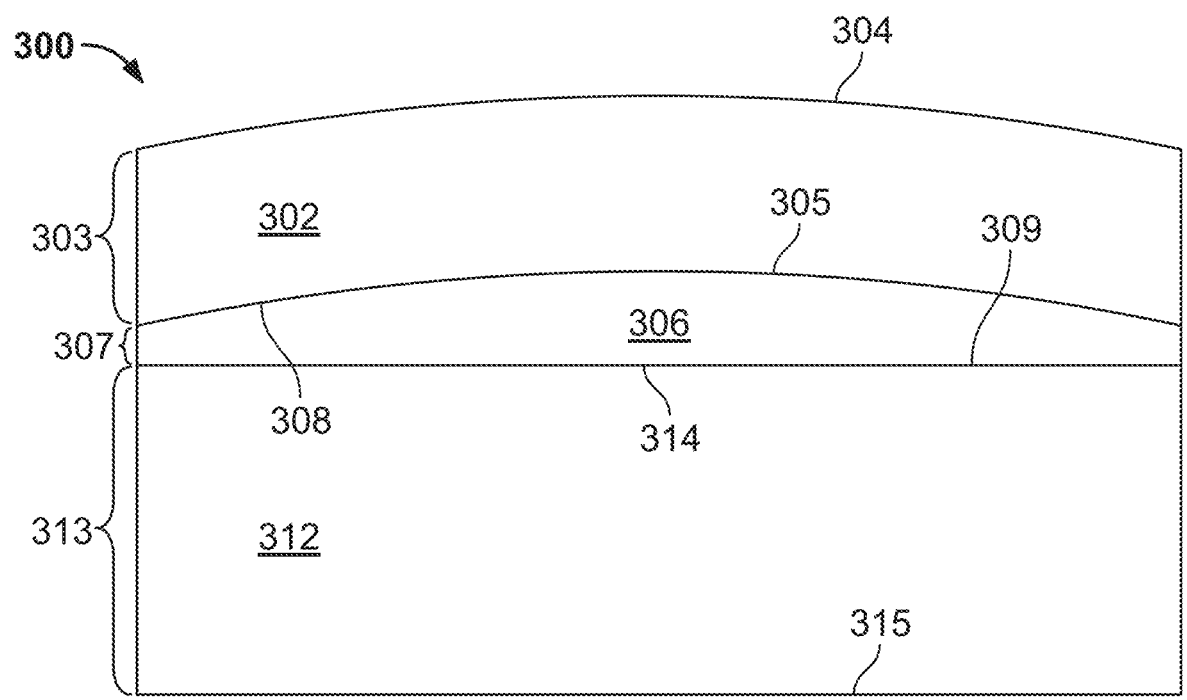
FIG. 3B is a cross-sectional view of the three-layered biomimetic osteochondral implant of FIG. 3A.
Figure 4A:
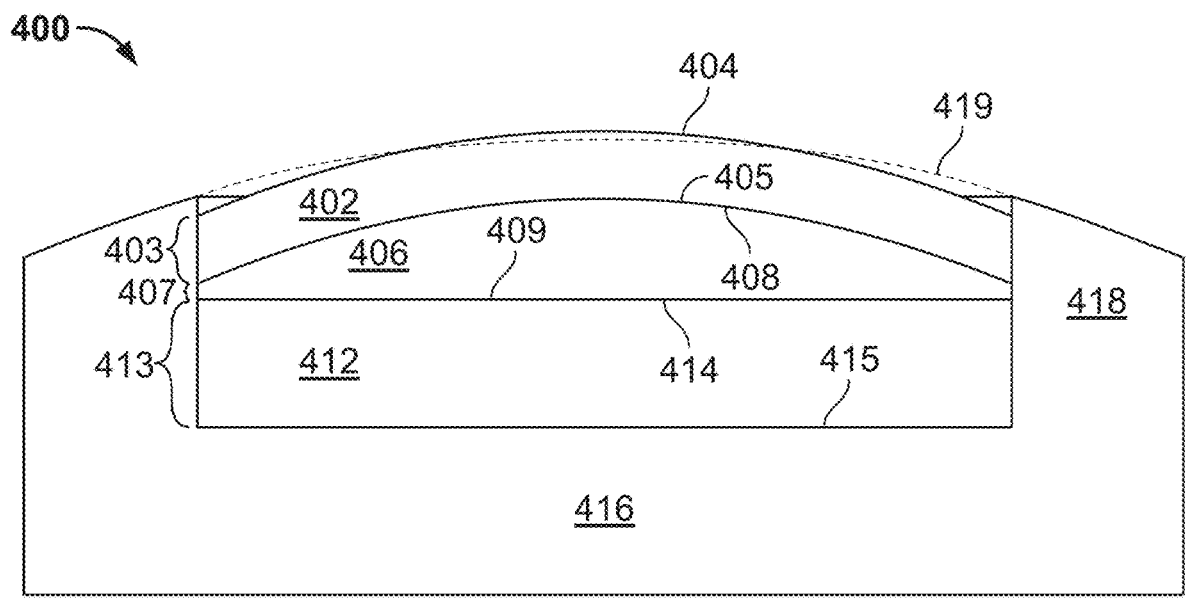
FIGS. 4A and 4B depict an biomimetic osteochondral implant, according to an illustrative implementation, after insertion into an implantation site having a convex articular surface. In this implementation, the edge of the compliant surface is offset from the cartilage surface while the center of the implant protrudes outwards from the native joint surface, such that the offset varies across the compliant surface. The dotted line represents the native joint surface.
Figure 4B:
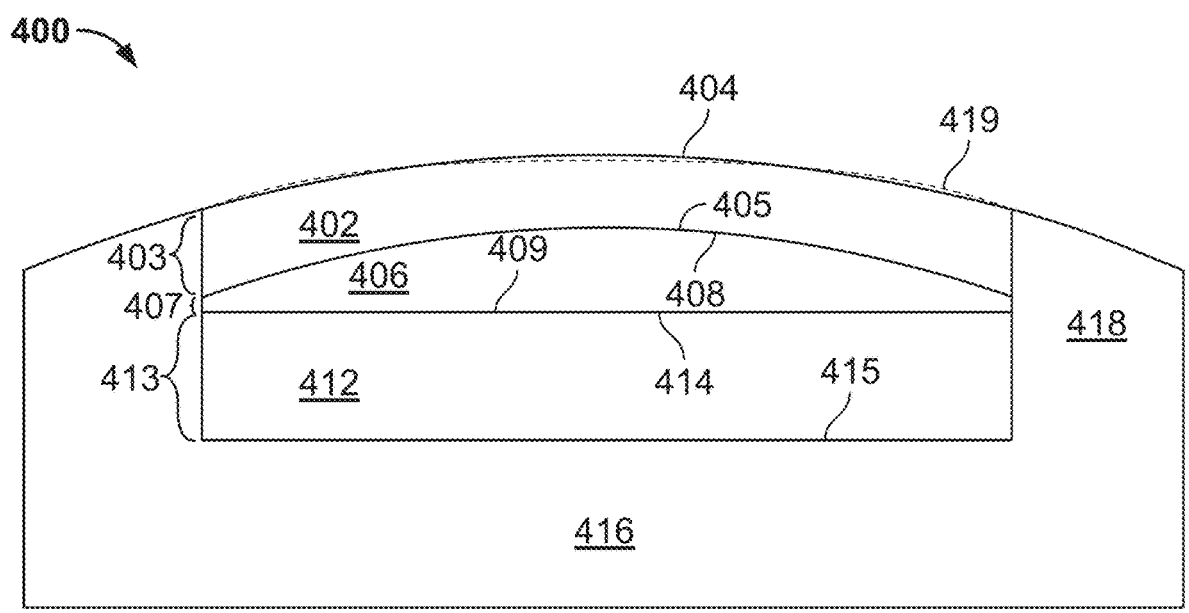

In some implementations, second thickness 107 is variable with a first height extending between second surface 109 and first surface 108 at a first position along first surface 108 and a second height extending between second surface 109 and first surface 108 at a second position along first surface 108. The first height may have a maximum at a position along perimeter 110 and the second height has a maximum at a position within external face 111. For example, the second height with the maximum at the position within external face 111 may be aligned coaxially with the axis of bearing zone 102, the axis of middle zone 106, or the axis of base zone 112. As mentioned above, external face 111 may be convex or concave, but second surface 109 may be flat, such that middle zone 106 is plano-convex (e.g., as shown in FIGS. 3B, 4A, and 4B) or plano-concave (e.g., as shown in FIGS. 6A and 6B), respectively. There may be a tapered region extending along external face 111 from the maximum second height toward perimeter 110. The first height maximum may be higher than the second height maximum, such that the tapered region forms a concave contour/curve. Alternatively, the first height maximum is lower than the second height maximum, such that the tapered region forms a convex contour/curve. External face 111 may include a ridge region extending radially across external face 111. A plurality of ridges may protrude into under surface 105. In some implementations, external face 111 includes multiple regions with differing respective radii of curvature. For example, the regions include a combination of two or more of flat, concave, convex, slanted, ridged, or pointed surfaces.

Implant 100 and perimeter 110 may have various shapes. The shape may be chosen to surround or enclose a lesion in the cartilage of a joint, such as a diarthrodial joint. Suitable shapes for implant 100 and perimeter 110 are illustrated in FIGS. 7A-7D and 14A-14J; however, other shapes may be used as appropriate for the size and shape of a given lesion or site for repair using implant 100. Perimeter 110 may include a curved edge extending circumferentially about the central axis of implant 100.

Implant 100 may also have various sizes, and accordingly the various zones may vary in size according to different implementations. For example, first thickness 103, second thickness 107, or third thickness 113 may each have one or more heights of between 0.01 mm and 25 mm, 1 mm and 20 mm, 5 mm and 15 mm, 3 mm and 4.5 mm, 5 and 10 mm, about 1 mm, about 5 mm, about 10 mm, or about 15 mm. As discussed above, second thickness 107, or the other thicknesses, may also vary in height. First thickness 103, second thickness 107, or third thickness 113 may each have a boundary height of 0.01 mm to 10 mm at a position along perimeter 110. The boundary height may be 0.1 mm to 5 mm, 0.2 to 5 mm, 1 to 5 mm, about 1 mm, about 2 mm, about 3 mm, about 4 mm, or about 5 mm. In some implementations, the first height is about 1 mm. In some implementations, first thickness 103, second thickness 107, or third thickness 113 tapers toward perimeter 110 such that the boundary height is less than 0.1 mm, but the implant 100 has a thickness positioned inside the boundary, away from the perimeter, which is much higher than the boundary height, for example between 2 and 10 times higher than the boundary height. The thickness may alternatively taper inward such that the boundary height is taller than the height of the interior thickness inside the boundary. Bearing zone 102 and middle zone 106 may extend axially from outer base surface 114 to compliant surface 104 over an axial length of 1 mm to 10 mm, 2 mm to 8 mm, 4 mm to 6 mm, or about 5 mm. Implant 100 may have a width (or its perimeter 110 may encompass an area) of 5 mm to 25 mm, 5 mm to 15 mm, or about 10 mm, and may be aligned to perpendicularly intersect the central axis.

Figure 10:
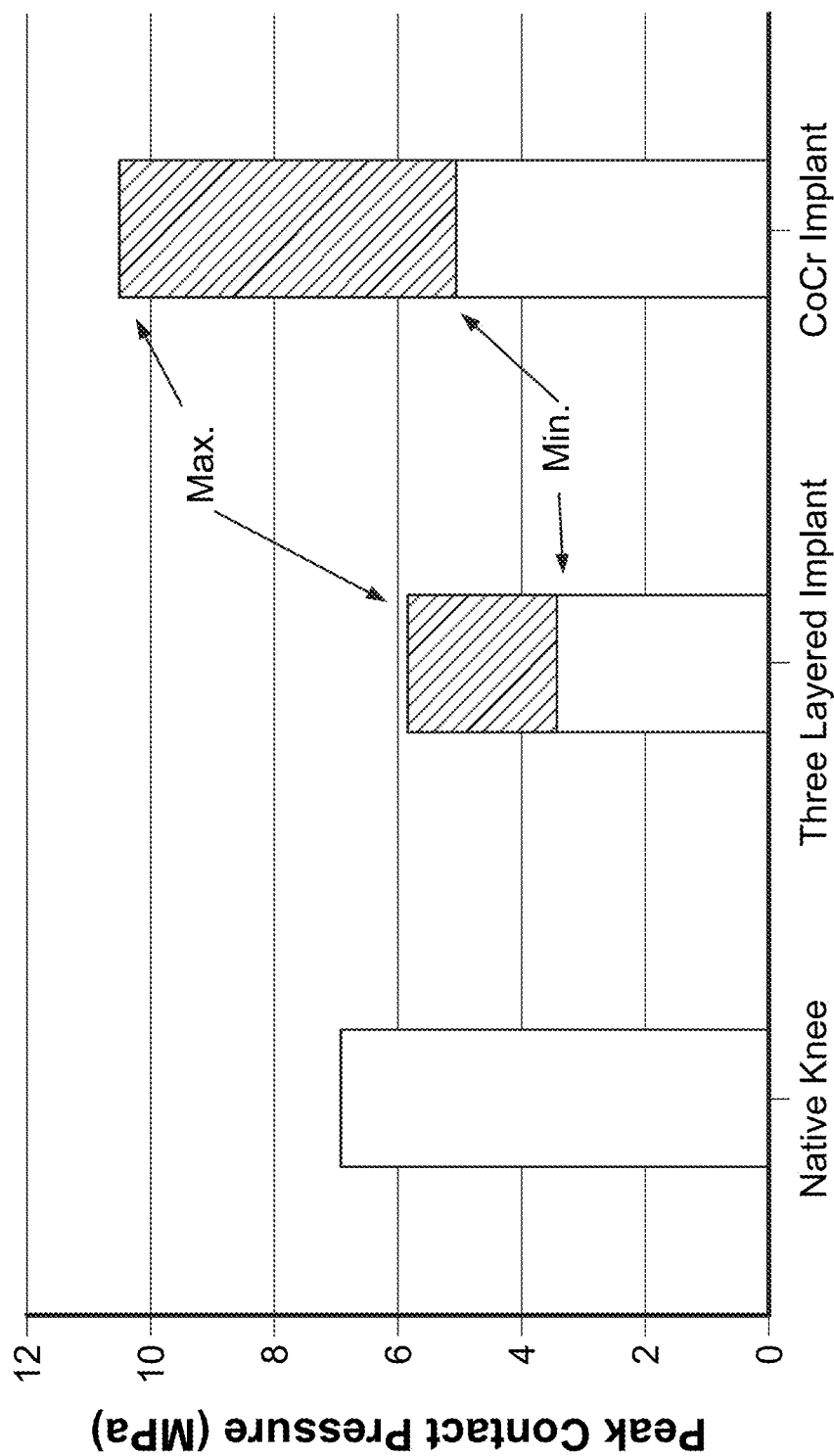
FIG. 10 shows a chart of peak contact pressures of various implants with a cartilage lesion on the medial condyle of the femur; the native knee results are those with no lesion or implant in place; the three-layered implant results illustrate the pressure after implantation with a three-layered biomimetic osteochondral implant according to an illustrative implementation of the present disclosure; and the CoCr results are after implanting an implant with a CoCr articular surface of the same geometry as the three-layered biomimetic osteochondral implant.

As noted above, the stiffness of middle zone 106 is greater than the stiffness of bearing zone 102, and the stiffness of base zone 112 is greater than the stiffness of the middle zone, thereby providing a stiffness gradient that increases from the bearing zone to the base zone, similar to what may be found in normal cartilage and osteochondral units. The variation in stiffness between zones can be quite high. In some implementations, the bearing zone stiffness is 40 MPa to 150 MPa. In some implementations, the middle zone stiffness is 50 MPa to 500 MPa, while in some implementations, the base zone stiffness is 1.5 GPa to 11 GPa. In some implementations, the middle zone stiffness is at least 1 to 20 times, 1 to 15 times, 1 to 10 times, 1 to 5 times, 5 to 10 times, 10 to 15 times, 15 to 20 times, about 1.25 times, about 2 times, about 5 times, about 10 times, about 15 times, or about 20 times the bearing zone stiffness. In some implementations, the base zone stiffness is at least 3 to 25 times, 5 to 20 times, 5 to 15 times, 5 to 10 times, 10 to 15 times, 15 to 20 times, 20 to 25 times, about 3 times, about 5 times, about 10 times, about 15 times, about 20 times, or about 25 times the second stiffness. Any of the first stiffness, second stiffness, and third stiffness may have a stiffness gradient extending therethrough. For example, bearing zone 102 may have a stiffness gradient extending from under surface 103 to the compliant surface 104 of greater than or equal to 1 kPa/mm. Stiffness gradients may be less than or equal to 0.1 kPa/mm, 1 kPa/mm, 5 kPa/mm, or 10 kPa/mm, or greater. High relative differences in stiffness between the zones can cause poor distribution of physiological loads when applied by the opposing joint surface to the implant 100 (see FIG. 10), leading to increased risk of damage to implant 100 or surrounding native tissue. Creation of a more gradual stiffness gradient across the layers and one that matches the surrounding tissue allows for loads to be better distributed throughout implant 100 and in conjunction with the native tissue, so as to produce a smooth transition between the implant and the surrounding tissue, and distribute force laterally within the implant so as to stabilize the axial structure of the implant. In certain implementations, the bearing zone 102 has an average stiffness of about 100 MPa, the middle zone 106 has an average stiffness of about 250 MPa, and the base zone 112 has an average stiffness of about 5 GPa.

Implant 100 is suitable for cartilage repair at various sites in the body, such as the articular cartilage within diarthrodial joints (e.g., knee, hip, ankle, toe, thumb, wrist, elbow, shoulder). Suitable sites include the distal femur, proximal tibia, patella, distal tibia, distal fibula, calcaneus, talus, tibiofibular joint, proximal humerus, glenoid, proximal femur, pelvis, distal humerus, proximal ulna, proximal radius, distal radius, distal ulna, carpals, distal metacarpal, proximal phalanx, and other cartilage known to those skilled in the art. Other articulating joint surfaces that can be repaired with the techniques disclosed hereininclude the spinal disc (nucleus pulposus), vertebral facets, and the meniscus in the knee. Implant 100 is suitable for implantation in humans as well as other organisms having cartilage, particularly articular cartilage.

Implant 100 may be designed to deform to a certain amount under physiological loads by adjusting the compressive modulus in any or all of the zones. For example, bearing zone 102 can be configured with the ability to deform between 2% and 25% under physiological load, with repeatable recovery of >70% of the deformation when said load is removed. Middle zone 106 may be configured to deform between 2% to 10% under physiological load, with repeatable recovery of greater than or equal to 70% of the deformation when the physiological load is removed. When the bearing layer and middle layer are attached, implant 100 may have the ability to deform between 5% to 20% under physiologic load, with repeatable recovery of greater than or equal to 80%. In some implementations, the repeatable recovery is greater than or equal to 95%. For the knee in particular, typical peak physiological loads through the knee joint include 2-4 bodyweights (e.g., 3.1 BW) during walking, 4-6 bodyweights for jogging (e.g., 5.5 BW), 2-5 bodyweights during sit-stand-sit, 4-6 bodyweights during stair climbing, and 7-12 bodyweights during running. See, e.g., Bergmann G, Bender A, Graichen F, et al. Standardized loads acting in knee implants. *PLoS One.* 2014; 9(1) (doi: 10.1371/journal.pone.0086035); see also, e.g., ASTM F3141-17a Standard Guide for Total Knee Replacement Loading Profiles. Accordingly, implant 100, when implanted in the knee joint, follows the above-mentioned deformations under these peak physiological loads on the knee joint.

An implant may be axisymmetric or symmetric along one or more vertical planes. For instance, it can be cylindrical with a dome shape on its outer surface with a single radius of curvature. Alternatively, it can have two or more radii of curvature. For instance, in some implementations, the implant can have a radius of curvature in one plane, and a larger radius of curvature in a perpendicular plane, thus making it more "sloped" in one direction and less sloped in the perpendicular plane. In a natural joint surface such as the condyle of the knee, there can be two major curvature planes, one that runs along the flexion/extension axis of the knee (which we will refer to as "the major radius"), and the other that is perpendicular to this plane, which has a smaller radius of curvature ("the minor radius"). These radii of curvature may also vary depending on the exact location on the joint surface. For example, an implant may be placed within an osteochondral defect that approximates the curvature(s) of the surrounding joint surface. Over time within the joint, the compliant surface or bearing zone reshapes under physiologic loads, reshapes such that the lubricious top surface takes on the radius or radii of curvature of the surrounding joint surface (FIGS. 4A/4B and 5A/5B). The biomimetic osteochondral implants of the present disclosure can adapt to any joint geometries, including substantially convex joint surfaces, substantially concave joint surfaces, substantially flat joint surfaces, or joint surfaces that have both convex and concave curvatures. Thus, the implant can, e.g., start convex and become more convex, flat, or concave depending on the shape of the surrounding joint surface; start flat and become concave or convex; or start concave and become even more concave (more steeply curved). In any way, the implant can be designed such that the surface contours of the implant match the native surface contours upon physiological loading.

An axisymmetric implant having a single radius of curvature may be inserted into an implantation site in which the natural cartilage has a radius of curvature that differs from that of the implant. Post-implantation, the compliant surface or bearing zone of the implant reshapes under physiologic loads, and the radius of curvature of the implant substantially matches the radius of curvature of the natural cartilage, which results in a smooth continuity of curvature for the repaired joint in all directions on and around the implant.

In some implementations, an axisymmetric implant having a single radius of curvature is inserted into an implantation site in which the natural cartilage has two radii of curvature that differ from that of the implant. Post-implantation, the compliant surface or bearing zone of the implant reshapes under physiologic loads and defines two radii of curvature that match the radii of curvature of the natural cartilage, which results in a smooth continuity of curvature for the repaired joint on and around the implant.

In some implementations, an implant having two different, perpendicular radii of curvature is inserted into an implantation site in which the natural cartilage has two radii of curvature that differ from those of the implant. Post-implantation, the compliant surface or bearing zone of the implant reshapes under physiologic loads and defines two radii of curvature that match the radii of curvature of the natural cartilage, which results in a smooth continuity of curvature for the repaired joint on and around the implant.

Figure 2A:
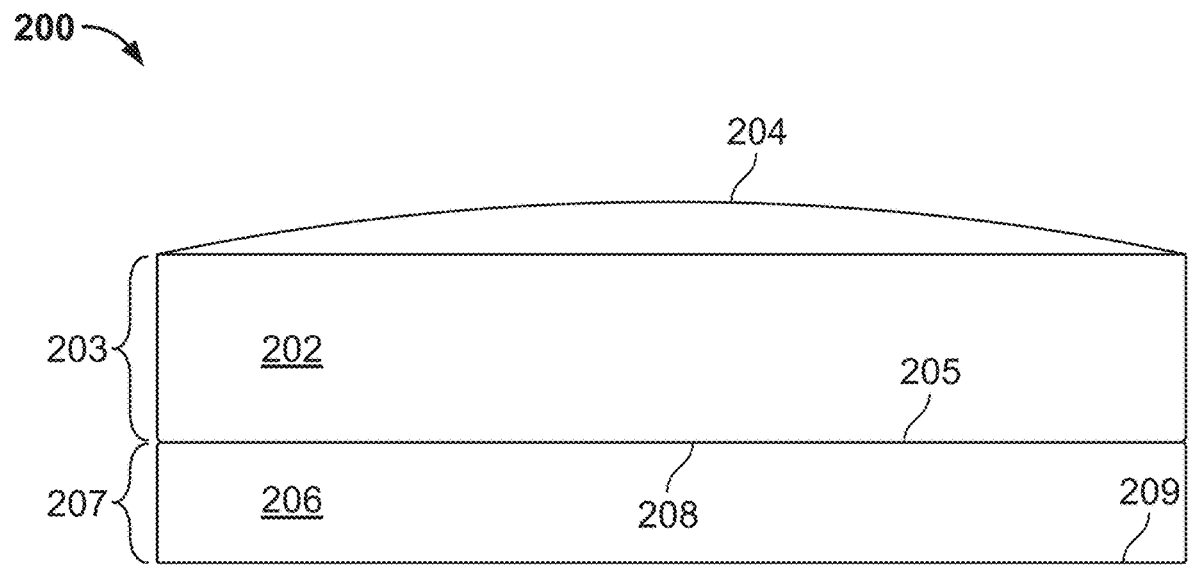
FIG. 2A depicts a two-layered biomimetic osteochondral implant, according to an illustrative implementation.
Figure 2B:
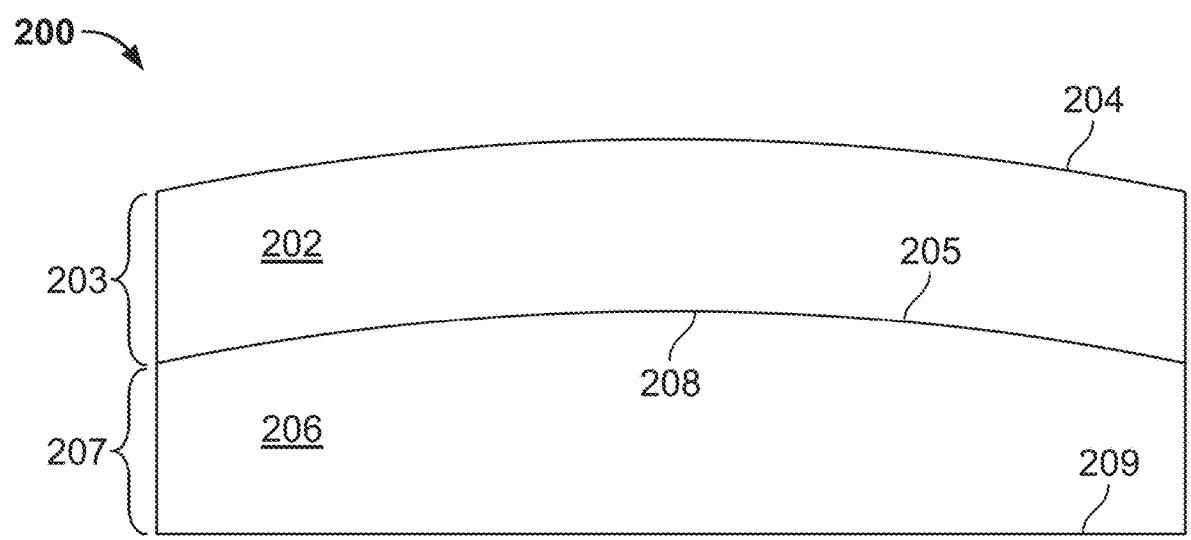
FIG. 2B is a cross-sectional view of the two-layered biomimetic osteochondral implant of FIG. 2A.

While FIGS. 1A-1C are shown having three zones, it should be understood that the multi-layered implants provided herein may have fewer than or more than three layers. FIG. 2A depicts a two-layered biomimetic osteochondral implant 200, according to an illustrative implementation; and FIG. 2B is a cross-sectional view of the two-layered biomimetic osteochondral implant 200 of FIG. 2A. Implant 200 comprises a bearing zone 202 and a base zone 206. Bearing zone 202 has a first thickness 203, a compliant surface 204, and an under surface 205. Base zone 206 has a second thickness 207, an outer base surface 208, and an inner base surface 209. While FIGS. 2A and 2B show compliant surface 204, under surface 205, and outer base surface 208 having a convex shape, giving implant 200 an overall plano-convex shape, it should be understood that implant 200 can be formed to have concave or flat surfaces, such that implant 200 is plano-concave or planar, respectively. Each of the zones and surfaces in implant 200 may have any of the elements or properties of those in implant 100 described in the foregoing. While implant 200 appears to have a cylindrical or elliptical cylindrical shape, it should be understood that implant 200 may have other shapes, including but not limited to any of the shapes shown in FIGS. 7A-7D and 9A-9J.

Figure 3A:
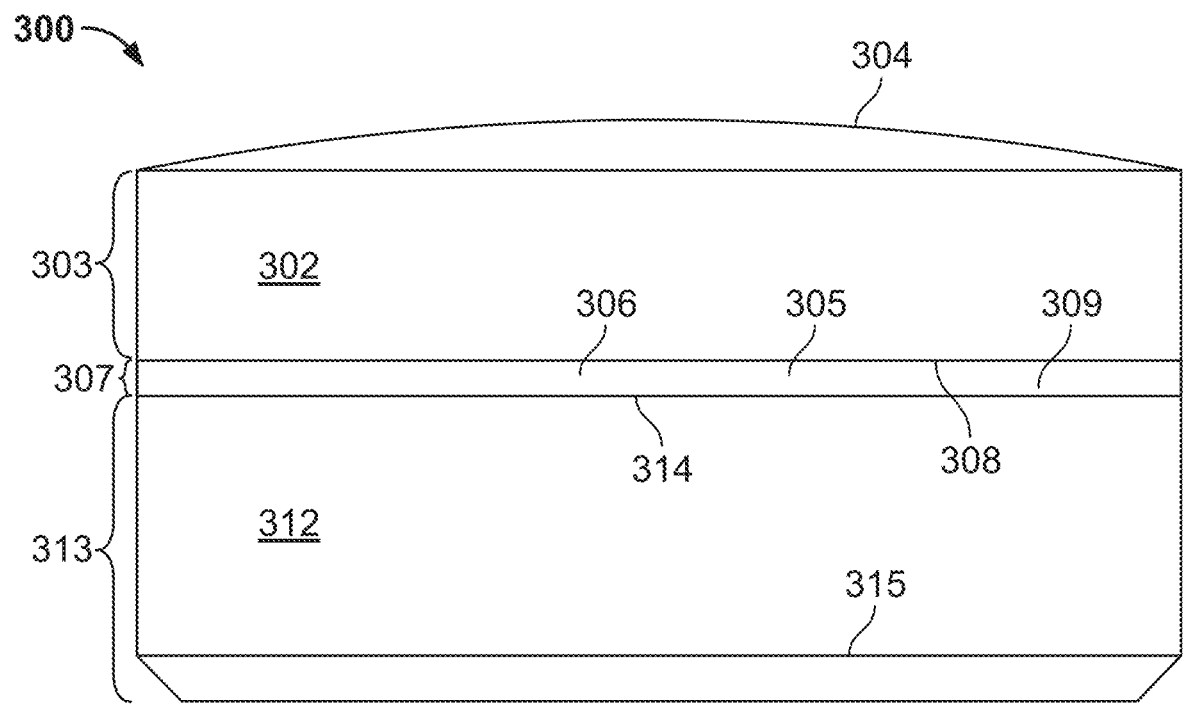
FIG. 3A depicts a three-layered biomimetic osteochondral implant according to an illustrative implementation.

FIG. 3A shows a three-layered biomimetic osteochondral implant 300, according to an illustrative implementation; FIG. 3B shows a cross-section of implant 300. Implant 300 comprises a bearing zone 302, a middle zone 306, and a base zone 312. Bearing zone 302 has a first thickness 303, a compliant surface 304 configured to interface with an opposing articular surface, and an under surface 305. Middle zone 306 has a second thickness 307, a shaped first surface 308 attached to under surface 305, and a second surface 309. Base zone 312 has a third thickness 313, an outer base surface 314 attached to second surface 309, and an inner base surface 315 configured to interface with bone. Under surface 305 conforms to shaped first surface 308, which has a convex shape, such that bearing zone 302 and compliant surface 304 taken on a convex shape. While FIGS. 3A and 3B show compliant surface 304, under surface 305, and shaped first surface 308 having a convex shape, giving implant 300 an overall plano-convex shape, it should be understood that implant 300 can be formed to have concave or flat surfaces, such that implant 300 is plano-concave or planar, respectively. Each of the zones and surfaces in implant 300 may have any of the elements or properties of those in implant 100 described in the foregoing. While implant 300 appears to have a cylindrical or elliptical cylindrical shape, it should be understood that implant 300 may have other shapes, including but not limited to any of the shapes shown in FIGS. 7A-7D and 9A-9J.

FIGS. 4A and 4B show a three-layered biomimetic osteochondral implant 400 that has been implanted into an osteochondral site comprising native tissue 418 (e.g., articular cartilage) and bone 416. Implant 400 comprises a bearing zone 402, middle zone 406, and base zone 412. Bearing zone 402 has a first thickness 403, a compliant surface 404, and an under surface 405. Middle zone 406 has a second thickness 407, a shaped first surface 408, and a second surface 409. Base zone 412 has a third thickness 413, an outer base surface 414, and an inner base surface 415 anchored to the bone 416. Native tissue 418 has a native tissue surface line 419, represented by the dashed line in FIGS. 4A and 4B. Each of the zones and surfaces in implant 400 may have any of the elements or properties of those in implant 100 described in the foregoing. While implant 400 appears is shown in two dimensions, it should be understood that implant 400 may have any of a variety of three-dimensional shapes, including but not limited to any of the shapes shown in FIGS. 7A-7D and 9A-9J.

FIG. 4A shows that implant 400, after having been implanted and anchored to bone 416, is offset from the native tissue surface line 419. At the edges of implant 400, compliant surface 404 sits below native tissue surface line 419, and at the center of implant 400, compliant surface 404 protrudes above native tissue surface line 419. This offset produces a mismatch in conformity, relative to the native tissue 418, when articulated with an opposing joint surface.

The mismatch in conformity strategically allows implant 400 to approximate the native tissue surface line 419 during or after physiological loading. Thus implant 400 closely articulates with the opposing joint surface in continuity with the surrounding native tissue 418, giving an advantageous mimetic effect that minimizes long-term damage to implant 400 or the surrounding native tissue 418.

Figure 5A:
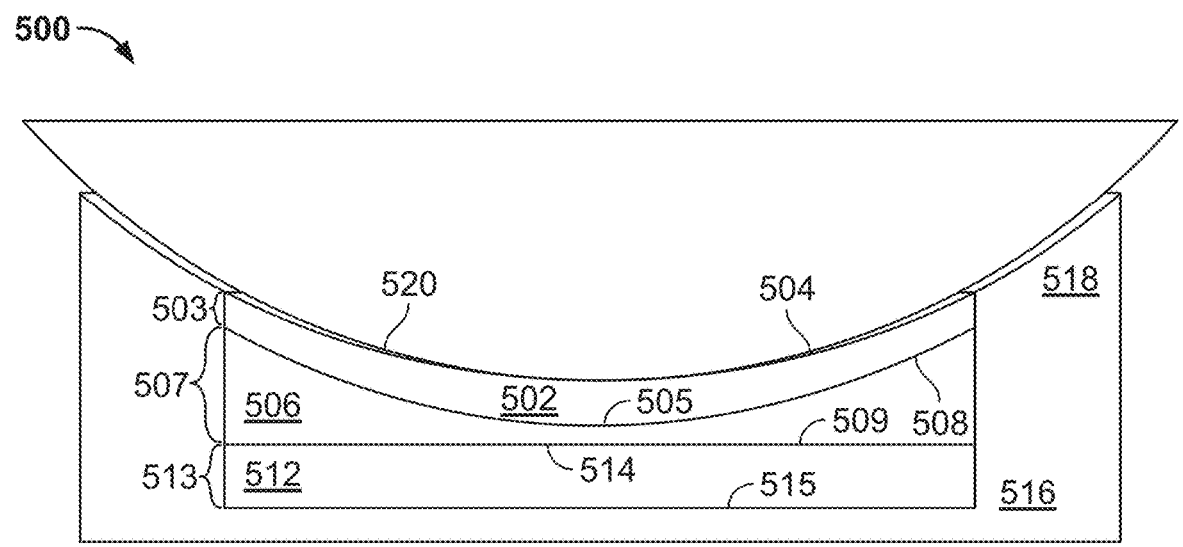
FIGS. 5A and 5B depict an biomimetic osteochondral implant, according to an illustrative implementation, after insertion into an implantation site having a concave articular surface.
Figure 5B:
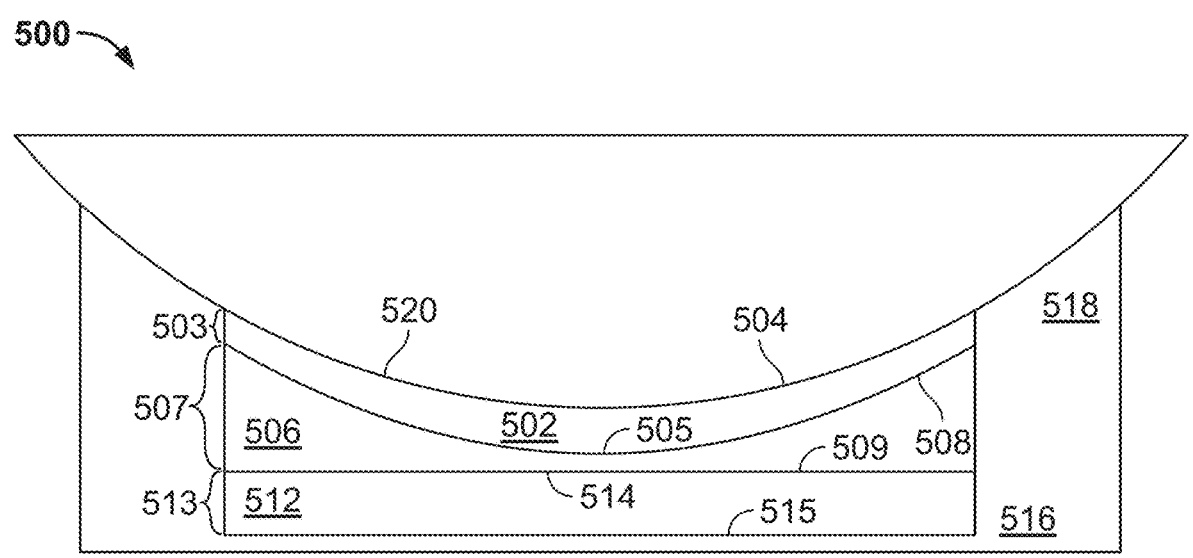

FIGS. 5A and 5B illustrate how the same effect is achieved when using a concave biomimetic osteochondral implant 500. Implant 500 comprises a bearing zone 502, middle zone 506, and base zone 512. Bearing zone 502 has a thickness 503, a compliant surface 504, and an under surface 505. Middle zone 506 has a thickness 507, a shaped first surface 508, and a second surface 509. Base zone 512 has a thickness 513, an outer base surface 514, and an inner base surface 515 anchored to the bone 516. An opposing joint surface 520, concave in shape, is positioned above compliant surface 504. Each of the zones and surfaces in implant 500 may have any of the elements or properties of those in implant 400 described in the foregoing. While implant 500 is shown in two dimensions, it should be understood that implant 500 may have any of a variety of three-dimensional shapes, including but not limited to any of the shapes shown in FIGS. 7A-7D and 9A-9J.

In FIG. 5A, implant 500 is implanted, the physiological load of the opposing joint surface 520 is not yet applied. Before loading, the compliant surface 504 at the outer edge of implant 500 sits at or below the surface of native tissue 516, and the compliant surface 504 at the center of implant 500 is thicker, causing a similar mismatch in conformity with the opposing surface 520 as discussed above.

FIG. 5B illustrates how, as the physiological load is applied via opposing joint surface 520, implant 500 conforms to the native tissue line of native tissue 518, allowing implant 500 to closely articulate with opposing joint surface 520. This has the advantage of minimizing long-term damage to implant 500 and the surrounding cartilage during physiological loading. For example, a biphasic polymer forming the bearing zone can have a plurality of structural molecules (e.g., polymeric chains) and a water composition which redistribute within the bearing zone upon compression (i.e., by the opposing joint surface) such that the mechanical load is distributed evenly across the implant.

FIGS. 6A and 6B illustrate example three-dimensional shapes of an implant 600 (or shapes of a portion of implant 600, e.g., the compliant surface 604). In each example, implant 604 has a compliant surface 604 and is implanted in an osteochondral site. Native tissue 618 at least partially surrounds (e.g., encompasses, forms a contact interface along the perimeter, or encloses the sides of) implant 600, which is anchored to bone 616. Implant 600 is multi-layered, for example, two- or three-layered, as described in the foregoing. Implant 600 may have any of the zones or properties thereof described in any of the foregoing examples (such as implant 100 of FIG. 1). Implant 600 is shown in a representative convex joint surface 618 but can be adjusted to suit any curvature of native tissue.

FIG. 6A demonstrates a circular-shaped implant 600 (or at least circular-shaped compliant surface 604). The circular implant 600 may be particularly useful for repair of point defects in articular cartilage. The circular implant 600 may have surfaces with concave, flat, convex, or any combination thereof geometries, as needed to suit a particular context (e.g., for a particular joint or surface of a joint).

FIG. 6B demonstrates an oval- or elliptical-shaped implant 600 (or at least an oval- or elliptical-shaped compliant surface 604). The oval or elliptical implant 600 may be particularly useful for repair of defects in articular cartilage that extend across the cartilage surface in one or more directions. The oval or elliptical implant 600 may have surfaces with concave, flat, convex, or any combination thereof geometries, as needed to suit a particular context (e.g., for a particular joint or surface of a joint). Joint repair implants and procedures as disclosed herein may be applied in a partial joint repair procedure (e.g., "uni" models that replace or resurface a portion (e.g., one condyle surface), multi-unit joint repair procedure (e.g., multiple condyle surfaces), or as a total repair procedure on one or both sides of the joint (e.g., a total knee procedure), where the implant is applied to both adjoining, articulating surfaces, In some implementations the implant (e.g., 600) may be useful for repairing large defects that extend radially across a large portion of the surface of the joint, for example across more than 5% of the articulating surface area of the joint, more than 10%, more than 20% or at least 50% of the articulating surface or more.

FIGS. 7A-7D represent further shapes for an osteochondral implant provided herein. Each of FIGS. 7A-7D is a top-down view of a compliant surface 704 of an implant 700, showing a two-dimensional view of the perimeter. Each shape may be selected based on the needs for different joints or defects. Any of the implants provided in the foregoing can be adjusted to these shapes. For example, a lesion may have a footprint across the native cartilage, and the shape of implant 700 may be selected so as to fully encompass the footprint of the lesion.

Figure 7A:
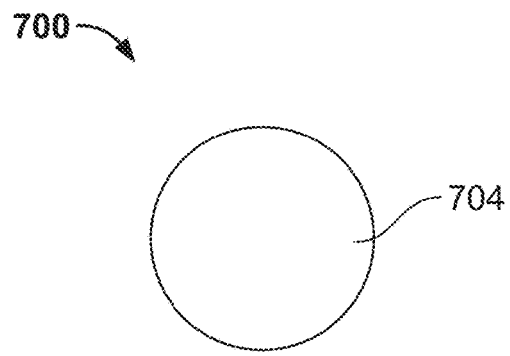
FIGS. 7A-7D depict implant shapes (or shapes of a portion of an implant, e.g., the lubricious top surface), according to illustrative implementations, which may be selected based on the needs for different joints or lesion sizes.
Figure 7B:
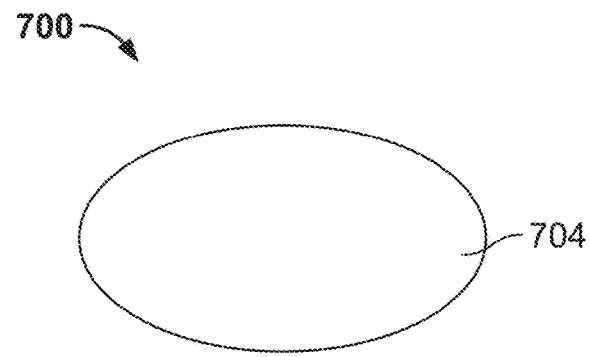
Figure 7C:
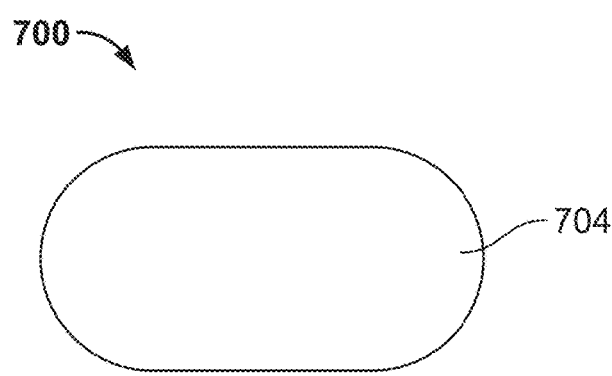
Figure 7D:
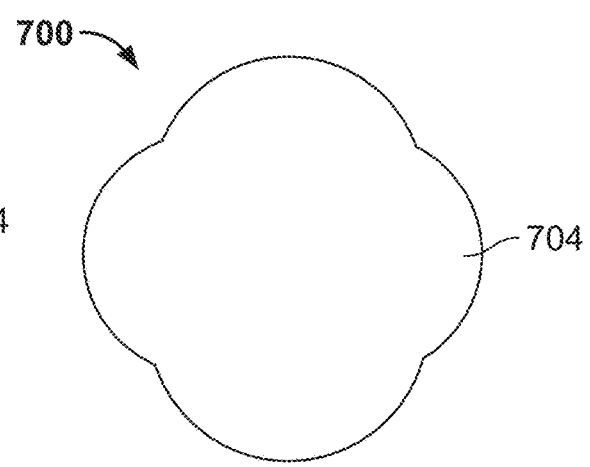

FIG. 7A illustrates a circular implant 700. FIG. 7B illustrates an elliptical implant 700. FIG. 7C illustrates an oval implant 700. FIG. 7D illustrates a "clover" shaped implant 700. The clover shape can be formed of two overlaid ellipses or ovals. Other suitable shapes include polygons, regular polygons, or amorphous shapes. Other implant shapes will become apparent to those skilled in the art upon review of the present disclosure.

FIGS. 8A-8I show cross-sectional views of various examples of attachment mechanisms 822 for use in the implants provided herein. In each example, attachment mechanisms 822 attaches a first layer 802 to a second layer 806, and may be a mechanical attachment, chemical bond, biological affixation, or any other suitable attachment. First layer 802 or second layer 806 can be any of the bearing zones, middle zones, base zones, base constructs, or bone described herein (i.e., any layers/zones in FIGS. 1A-5B). For example, attachment mechanism 822 may attach bearing zone 102 to middle zone 106 (i.e., between under surface 105 and shaped first surface 108), middle zone 106 to base zone 112 (i.e., between second surface 109 and outer base surface 114), or base zone 112 to bone 116 (i.e., between inner base surface 115 and bone 116). Any of the attachment mechanisms 822 may be combined to attach two or more layers in an implant. Some of the attachment mechanisms comprise multiple features (e.g., multiple posts, threads, spikes, overhangs, barbs, screws, hooks, adhesive spots, or other units of attachment). It should be understood that the attachment mechanism 822 may comprise at least 1, at least 2, at least 5, at least 10, at least 20, at least 30, at least 50, at least 100, at least 200, at least 500, or at least 1000 features (e.g., posts, threads, spikes, overhangs, barbs, screws, hooks, other forms of interdigitation, adhesive spots). The features may be dispersed across second layer 806 or first layer 802 in a regular pattern or may be randomly arranged so as to offer increased surface area for mechanical or biological attachment. The features may have pico-scale, nano-scale, micro-scale, or milli-scale dimensions. For example, the attachment mechanism 822 may have a height, width, or length of 1 to 1000 pm, 1 to 1000 nm, 1 to 1000 μm, or 1 to 20 mm. Attachment mechanisms 822 may be integrally formed in second layer 806 or configured as a separate construct.

Figure 8A:
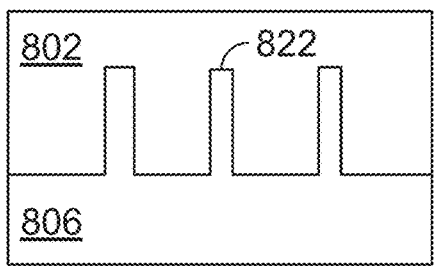
FIGS. 8A-8I depict various attachment mechanisms, according to illustrative implementations; the attachment mechanisms may be used to attach layers of the implant to each other or for attachment of the implant to bone.

FIG. 8A shows an attachment mechanism 822 comprising a post structure having a plurality of posts extending from second layer 806 into first layer 802 (or vice versa). For example, second layer 806 is base zone 112 of FIG. 1, with posts extending from inner base surface 115 into bone 116, which is first layer 802, upon implantation and anchoring. In some implementations, the posts extend into pre-fabricated cavities in first layer 802 using a press-fit. Alternatively, the posts may be configured to penetrate into first layer 802 and form cavities. The posts may comprise spikes, overhangs, barbs, threads, or hooks, as shown and elaborated in FIGS. 8C-8G. The posts may extend straight into first layer 802 or have a curvature or angle. For example, the posts may interdigitate (e.g., like fingers interlocking between two hands) within first layer 802, such that each post interlocks with at least one other post.

Figure 8B:
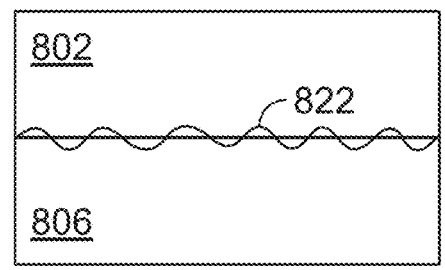

FIG. 8B shows an attachment mechanism 822 comprising a thread or wire attaching first layer 802 to second layer 806. Any suitable type of thread, wire, or suture may be used, such as surgical sutures or a shape-memory wire. The thread or wire may be sewn between first layer 802 and second layer 806, for example, using a needle or other suitable sewing mechanism. In some implementations, the thread or wire is introduced during fabrication or implantation of the implant and later removed after the layers have merged or attached to each other. For example, the second layer 806 is bone and first layer 802 is a porous base zone, and attachment mechanism 822 holds the layers together during implantation. After implantation, the bone grows into the porous base zone, such that the new growth anchors the implant, and attachment mechanisms 822 is no longer needed and can be removed.

Figure 8C:
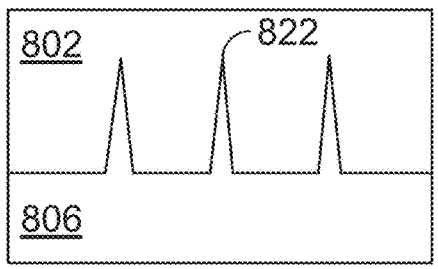

FIG. 8C shows an attachment mechanism 822 comprising a plurality of spikes extending from second layer 806 into first layer 802. The spikes may have the shape of a cylindrical pyramid, square pyramid, or other suitable shape. While the spikes are shown extending straight, the spikes may also be curved or flexible to penetrate and anchor into first layer 802. In some implementations, the spikes comprise overhangs, barbs, threads, or hooks (as shown in FIGS. 8D-8G).

Figure 8D:
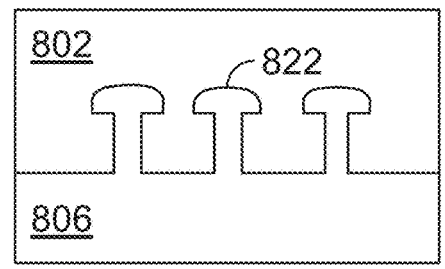

FIG. 8D shows an attachment mechanism 822 comprising a plurality of posts with overhangs extending into first layer 802 from second layer 806. The overhang posts may be shaped like mushrooms, with a "cap" extending radially outwards from the "stem". The overhangs serve to plug second layer 806 into first layer 802.

Figure 8E:
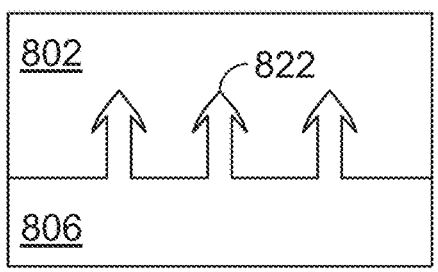

FIG. 8E shows an attachment mechanism 822 comprising a plurality of barbed posts extending from second layer 806 into first layer 802. The barbed posts as illustrated have two or more barbs, but it should be understood that the barbed posts may comprise at least one barb, at least two barbs, at least three barbs, at least four barbs, at least five barbs, or more.

Figure 8F:
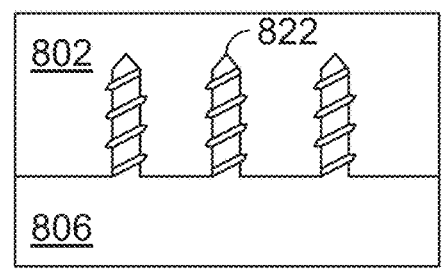

FIG. 8F shows an attachment mechanism 822 comprising a plurality of threaded posts or screws extending from second layer 806 into first layer 802. The screws may be machine screws (having a uniform diameter, not shown) or tapered screws (having a pointed tip as shown in FIG. 8F). Attachment 822 may further comprise threaded cavities for receiving the screws.

Figure 8G:
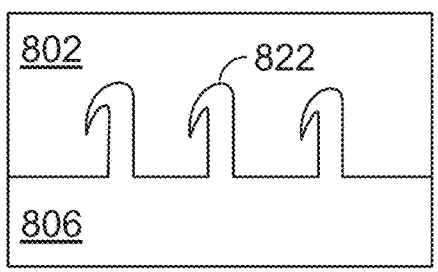

FIG. 8G shows an attachment mechanism 822 comprising a plurality of hooks extending from second layer 806 into first layer 802. The hooks are shown having one hook tip, but may be configured with a plurality of hook tips. First layer 802 may be configured with a receiving mechanisms, such as a plurality of sockets or loops which catch the hooks of attachment mechanism 822 during fabrication of implantation.

Figure 8H:
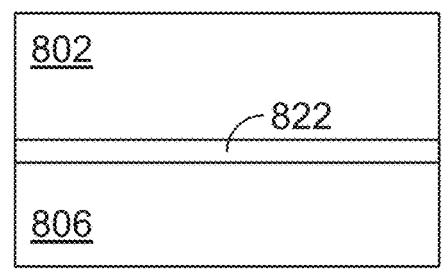

FIG. 8H shows an attachment mechanism 822 comprising an adhesive or bonding layer between first layer 802 and second layer 806. The adhesive or bonding layer may comprise an adhesive substance or bonding agent, examples of which are provided below, or may represent a chemical bond between substances used to construct first layer 802 and second layer 806. For example, the bonding layer represents covalent bonds between first layer 802 and second layer 806. Attachment mechanism 822 may comprise a continuous adhesive or bonding layer extending across at least 25%, at least 50%, at least 75%, or about 100% of a contact interface between first layer 802 and second layer 806. Alternatively, the adhesive or bonding layer comprises a plurality of spots of adhesive or bonds spaced apart between first layer 802 and second layer 806. Suitable bonding agents and adhesives are discussed below in the materials section.

Figure 8I:
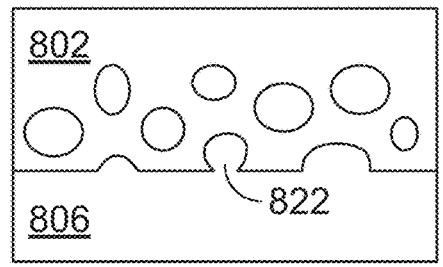

FIG. 8I shows an attachment mechanism 822 comprising a plurality of pores disposed in first layer 802. The pores allow for interdigitation with the opposing surface, for example during manufacturing of the implant or by bone/tissue growth into the pores post-implantation. The pores may be filled during manufacturing (e.g., by pouring a material at least partially constituting second layer 806 into the pores) or by material growth or creep into the pores over time. For example, second layer 806 may be bone (e.g., subchondral bone or cancellous bone), which grows into the pores in first layer 802, which may be the base of an implant, after the implant has been implanted onto the bone. At the surface of first layer 802 that interfaces with second layer 806, the plurality of pores may form a rough and randomized boundary. Pores may be advantageous for attachment due to the interdigitation of the first and second layers, which increases toughness of the attachment at the interface.

Additional attachment mechanisms not shown include bumps, pores, pillars, grooves, pyramids, or other forms of texturing a surface.

As discussed above in relation to FIGS. 1A and 1B, the biomimetic osteochondral implants provided herein may include one or more surfaces shaped to interface with an opposing joint surface (e.g., as the compliant or outward surface of a bearing zone, such as bearing zone 102) or as a middle surface configured to convey a shape into another layer (e.g., shaping the underside of a bearing zone, such as under surface 105 of bearing zone 102) disposed adjacent to said middle surface. FIGS. 9A-9J illustrate additional surface and implant shapes that may be used for certain joints or defects. The shapes in FIGS. 9A-9J may be applied to any of the layers or zones described herein.

Figure 9A:
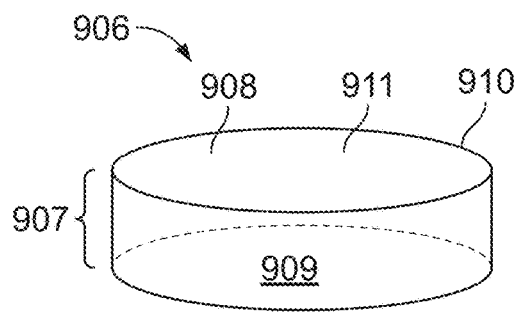
FIGS. 9A-9J show various shapes of surfaces for biomimetic osteochondral implants, according to illustrative implementations.
Figure 9B:
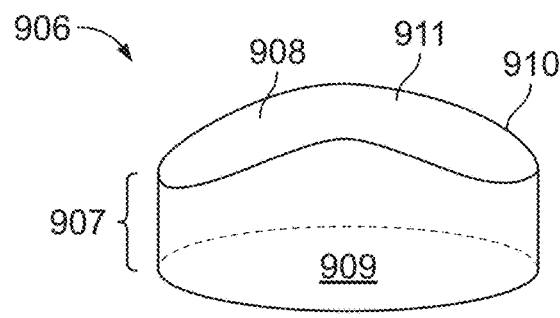
Figure 9C:
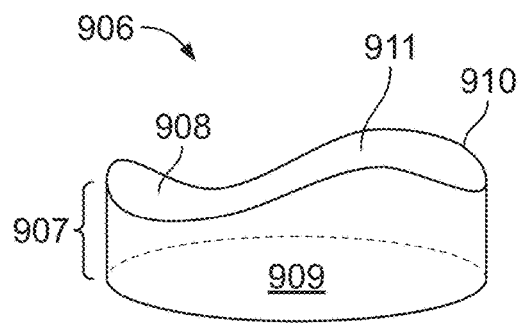
Figure 9D:
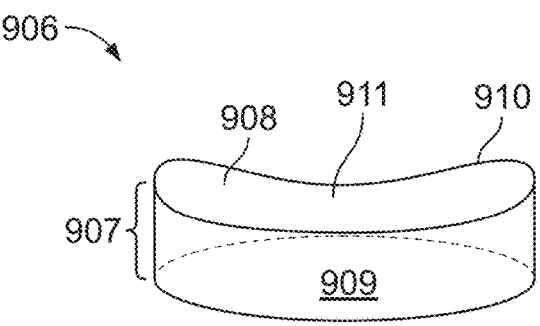

FIGS. 9A-9D show circular or elliptical layers 906 having a thickness 907, a shaped first surface 908 with perimeter 910 and a face 911, and a second surface 909 positioned opposite from the shaped first surface 908. In FIG. 9A, first surface 908 is flat, whereas first surface 908 in FIGS. 9B and 9D is convex and concave, respectively. It should be understood that the first surface 908 of FIGS. 9B and 9D may be oppositely curved in an opposing direction of the convex and concave curves to create a saddle shape. FIG. 9C shows an implementation where the surface 908 has a concave region and a convex region. Not shown is another implementation where both the first surface 908 and second surface 909 are flat, but face 911 is positioned diagonally (e.g., slanted) relative to second surface 909, such that the plane of first surface 908 intersects the plane of second surface 909 at some line. Another implementation not shown is a shaped first surface 908 having a saddle shape (i.e., convex along a first axis and concave along a second axis perpendicular to the first axis). Other shapes will be apparent to those skilled in the art or when designing an implant for a unique joint or defect.

Figure 9E:
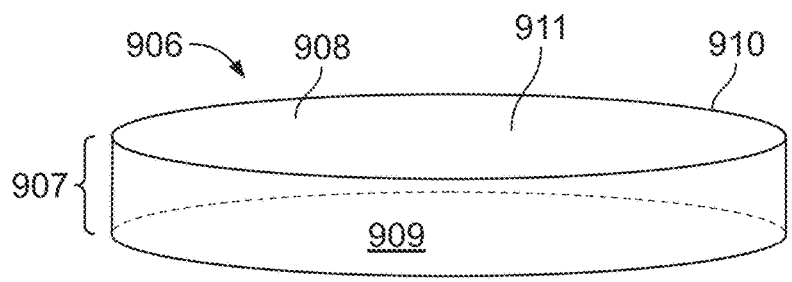
Figure 9F:
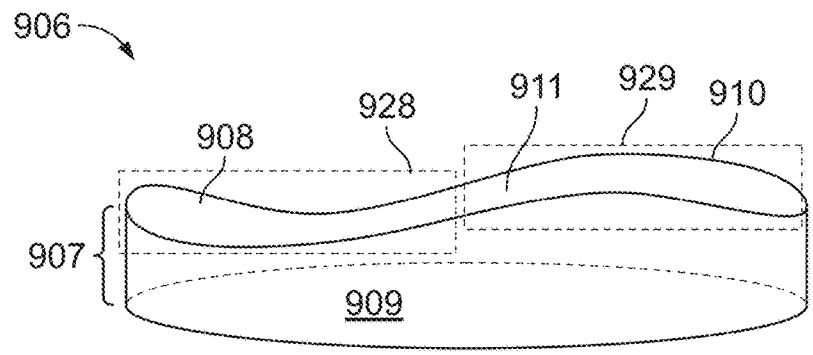

FIGS. 9E and 9F show elongated oval or elliptical layers 906 having a thickness 907, a shaped first surface 908 having a perimeter 910 and a face 911, and a second surface 909 positioned opposite from the shaped first surface 908. In FIG. 9E, first surface 908 is flat, whereas first surface 908 of FIG. 9F has a concave region 928 and a convex region 929. Oval or elliptical layers 906 may also have a first surface 908 having a solely concave, solely convex, slanted, or saddle-shaped face 911.

Figure 9G:
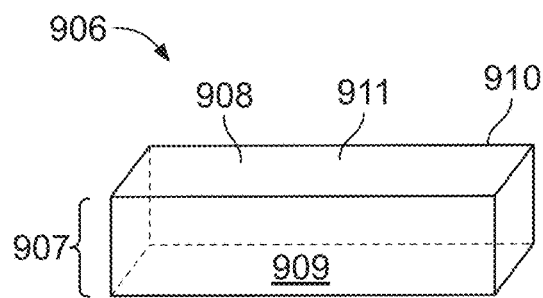
Figure 9H:
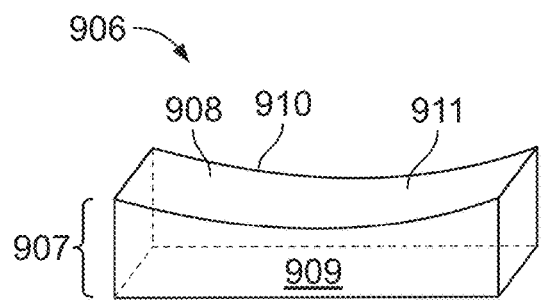
Figure 9I:
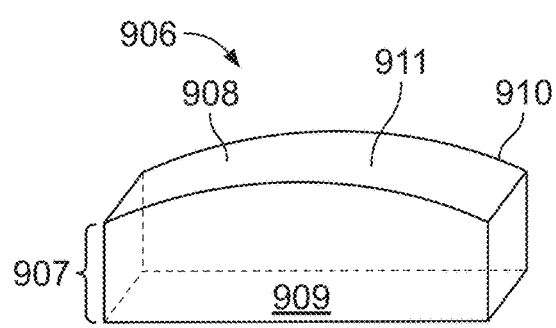
Figure 9J:
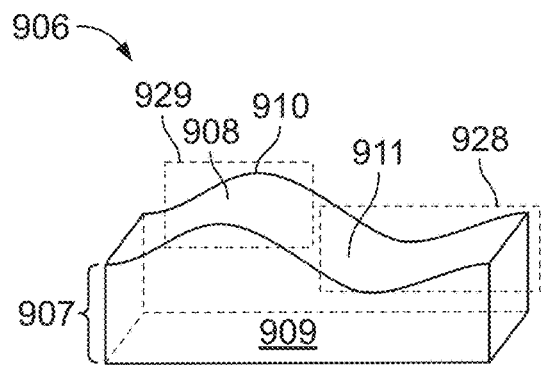

FIGS. 9G-9J show square or rectangular layers 906 having a thickness 907, a shaped first surface 908 having a perimeter 910 and a face 911, and a second surface 909 positioned opposite from the shaped first surface 908. FIG. 9G shows a flat first surface 908. FIGS. 9H and 9I show a concave and convex first surface 908, respectively. FIG. 9J has a first surface 908 with a concave region 928 and a convex region 929. Square or rectangular layers 906 may also have a first surface 908 having a slanted or saddle-shaped face 911.

Materials

As described in the foregoing, one or more layers of an biomimetic osteochondral implant, such as bearing zone 102 of implant 100 of FIG. 1A, may comprise a thermoplastic polymer, which, in some implementations, is flowable. Suitable thermoplastic polymers include, but are not limited to acrylonitrile butadiene styrene (ABS), polymethylmethacrylate (PMMA), celluloid, cellulose acetate, ethylene-vinyl acetate (EVA), ethylene vinyl alcohol (EVAL), Kydex, liquid crystal polymer (LCP), polyacetal (POM), polyacrylate (acrylic), polyacrylonitrile (PAN), polyamide (PA or Nylon), polyamide-imide (PAI), polyaryletherketone (PAEK), polyhydroxyalkanoates (PHAs), polyketone (PK), polyester, polyetheretherketone (PEEK), polyetherimide (PEI), polyethersulfone (PES), polyethylenechlorinates (PEC), polyimide (PI), polymethylpentene (PMP), polyphenylene oxide (PPO), polyphenylene sulfide (PPS), polyphthalamide (PPA), polystyrene (PS), polysulfone (PSU), polyvinyl acetate (PVA), polyvinyl chloride (PVC), polyvinylidene chloride (PVDC), Spectralon, styrene-acrylonitrile (SAN), polydimethylsiloxane (PDMS), and polyurethane (PU). A wide variety of polyurethanes can be used with varying hard segment, soft segment, and chain extender compositions, as will be described herein.

In some implementations, the thermoplastic polymer is a thermoplastic polyurethane-based polymer (e.g., polyether urethane, polycarbonate urethane, polyurethane urea, silicone polyether urethane, or silicone polycarbonate urethane) containing a network of hard segments and soft segments that may be swollen with a monomer and optional solvent, along with an initiator and cross-linker, such that the soft segments are swollen while mostly not affecting the hard segment material. This swelling process is not dissolution of the polymer; rather, the hard segments act as physical crosslinks to hold the material together as the soft segments are imbibed with the monomer(s) and optional solvent(s). After polymerization and cross-linking of the monomers, a second polymeric network is formed in the presence of the first network, creating an IPN or semi-IPN in which the second polymeric network (i.e., the polymerized monomer) is primarily sequestered within the soft, amorphous domain of the first polymer. Despite some degree of molecular rearrangement and further phase separation, the hard segments largely remain ordered and crystalline, providing structure and strength to the material. The new properties prepared by such a process depend on the properties of the polymerized monomers that were introduced and, in some implementations, modifications to the polymerized monomers (e.g., carboxylic-acid-containing monomers) that are subsequently introduced. Examples of such new properties include lubriciousness, conductivity, hardness, absorbency, permeability, photoreactivity, and thermal reactivity.

Any number of chemistries and stoichiometries can be used to create the polyurethane polymer. For example, the hard segment may be formed from 1,5-naphthalene diisocyanate (NDI), isophorone isocyanate (IPDI), 3,3-bitoluene diisocyanate (TODI), methylene bis(p-cyclohexyl isocyanate) (HMDI), cyclohexyl diisocyanate (CHDI), 2,6-toluene diisocyanate or 2,4-toluene diisocyanate (TDI), hexamethyl diisocyanate, or methylene bis(p-phenyl isocyanate); and the soft segment may be formed from polyalkylene oxides (e.g., polyethylene oxide (PEO), polypropylene oxide (PPO), and polybutylene oxide (PBO)), polybutadiene, polydimethylsiloxane (PDMS), polyethylene adipate, polycaprolactone, polytetramethylene adipate, polyisobutylene, polyhexamethylene carbonate glycol, poly(1,6-hexyl-1,2-ethyl carbonate). Any number of telechelic polymers can be used in the soft segment, if end-groups that are reactive with isocyanates are used. For instance, hydroxyl- or amine-terminated poly(vinyl pyrrolidone), dimethylacrylamide, carboxylate or sulfonated polymers, telechelic hydrocarbon chains (with hydroxyl and/or amine end groups), dimethylolpropionic acid (DMPA), or these in combination with each other or with other soft segments mentioned above (e.g., PDMS) can be used.

Chain extenders include, for example, 1,4-butanediol, ethylene diamine, 4,4'-methylenebis(2-chloroaniline) (MOCA), ethylene glycol, and hexane diol. Any other compatible chain extenders can be used alone or in combination. Crosslinking chain extenders can be used containing isocyanate-reactive end groups (e.g., hydroxyl or amine) and a vinyl-based functional group (e.g., vinyl, methacrylate, acrylate, allyl ether, or acrylamide) may be used in place of some or all of the chain extender. Examples include 1,4-dihydroxybutene and glycerol methacrylate. Alternatively, crosslinking can be achieved through the use of a polyol such as glycerol which contains greater than two hydroxyl groups for reaction with isocyanates.

In some embodiments, the monomer is a carboxylic-acid-containing monomer. Suitable carboxylic-acid-containing monomers used to form the second polymeric network include characteristics such as (1) being capable of swelling without dissolving the thermoplastic polymer (e.g., polyurethane) and (2) being polymerizable. Non-limiting examples include acrylic acid, methacrylic acid, crotonic acid, linolenic acid, maleic acid, fumaric acid, and combinations thereof. After optional swelling in a buffered aqueous solution, the second network of the mixed anion IPN or semi-IPN is ionized, and the mixed anion IPN or semi-IPN is water-swollen and lubricious. Thus, hydrophilicity (i.e., water absorbency) can be introduced into an otherwise hydrophobic material. A hydrophobic polymer material such as polyurethane or ABS can be infiltrated with various mixed anion polymers (e.g., polymers comprising a combination of underivatized carboxylic acid groups and derivatized carboxylic acid groups) such that it absorbs water. In some embodiments, an additional co-monomer is used to form the second polymeric network. The additional co-monomer may be ionic or non-ionic. Exemplary non-ionic monomers include, but are not limited to acrylamide, methacrylamide, N-hydroxyethyl acrylamide, N-isopropylacrylamide, methylmethacrylate, N,N-dimethylacrylamide, N-vinyl pyrrolidone, 2-hydroxyethyl methacrylate, 2-hydroxyethyl acrylate, and derivatives thereof.

Functional groups may be incorporated into an IPN or semi-IPN that including a second polymeric network including carboxylic acid groups by, e.g., replacing the pendant carboxylic acid groups present on a poly(carboxylic acid) (e.g., poly(acrylic acid) or poly(methacrylic acid)) in an IPN with functional groups. In some implementations, the functional groups are sulfonic acid groups, which can be incorporated into an IPN or semi-IPN comprising carboxylic acid groups by reacting the IPN or semi-IPN with a sulfonic-acid-containing compound, e.g., by reacting the carboxylic acid groups of the solid article with an amino sulfonic acid compound such that an amide bond is formed between the carboxylic acid groups of the poly(carboxylic acid) and the amine groups of the amino sulfonic acid compound. In some embodiments, the amino sulfonic acid compound is a compound of the formula (H2N)xR(SO3H)y or a salt thereof, where R is an organic moiety, where x is a positive integer, and wherein y is a positive integer. In certain implementations, x may range from 1 to 10, typically, 1 to 5 (i.e., x may be 1, 2, 3, 4 or 5) and y may range from 1 to 10, typically, 1 to 5 (i.e., y may be 1, 2, 3, 4 or 5). In some implementations, the compound of the formula (H2N)xR(SO3H)y has a hydrodynamic radius that allows the diffusion of the molecule within the IPN. R may be, for example, a hydrocarbon moiety, for example, a including linear, branched or cyclic hydrocarbon moiety, or a hydrocarbon moiety having a combination of two or more of linear, branched and cyclic hydrocarbon substituents. The hydrocarbon moiety may be, for example, C1-C12 hydrocarbon or a polymeric moiety including polymeric/oligomeric containing heteroatoms. In certain implementations, the hydrocarbon moiety may be selected from an alkane moiety, an alkene moiety, an alkyne moiety, an aromatic moiety, or a hydrocarbon moiety having a combination of two or more of alkane, alkene, alkyne, or aromatic components. In certain implementations, the amino sulfonic acid may be selected from taurine and taurine derivatives, including 1-substituted, 2-substituted, 1,1-disubstituted, 2,2-disubstituted, and 1,2-disubstituted taurines, such as 1-hydrocarbon-substituted, 2-hydrocarbon-substituted, 1,1-hydrocarbon-disubstituted, 2,2-hydrocarbon-disubstituted, and 1,2-hydrocarbon-disubstituted taurines, where the substituted hydrocarbons may be selected, for example, from the hydrocarbon moieties described above. In other implementations, the amino sulfonic acid compound is one that results in the formation of 2-acrylamido-2-methyl propane sulfonic acid or acrylamido ethane sulfonic acid.

Exemplary IPNs and semi-IPNs suitable for use as a layer and preparation procedures thereof are disclosed in, e.g., U.S. Pat. Nos. 8,883,915, 10,457,803, 10,752,168, 10,792,392, and 10,869,960, the entire contents of which are incorporated by reference for all purposes as if fully set forth herein.

As described in the foregoing, a middle layer of an implant, such as the middle zone 106 of implant 100 of FIG. 1A, is constructed with a polymer that has a greater stiffness than an outer layer that would interface and articulate within the joint.

In some implementations, a middle layer is formed from a first precursor and a second precursor. In some embodiments, the middle layer may be formed from one or more additional precursors. The first precursor has a first chemical functional group that allows it to form a covalent bond with a second precursor which has a second chemical functional group to form a copolymer. The first precursor, as well as the second and any additional precursors, may have one, two, three, or four or more chemical functional groups. The first, second, and any additional chemical functional groups on a precursor may be the same or they may be different. Functional groups on different precursors may be the same or may be different. In some implementations, a precursor has a chemical functional group that may form a covalent bond in response to a free-radical initiator or in response to another (e.g., an ionic/anionic) initiator. In some implementations, a chemical functional group may be an unsaturated group, such as an ethylenically unsaturated group (e.g., a vinyl group).

In some implementations, a chemical functional group may be an acrylic group and may have a carbon-carbon double bond and a carbon-oxygen double bond separated by a carbon-carbon single bond. An "acrylic" functional group may, for example, be derived from an α,β-unsaturated carbonyl compound. A molecule containing an acrylic group may be decorated with additional chemical moieties. Examples of acrylic groups that can be used in the precursors include, but are not limited to acrylic acid, methacrylic acid, hydroxyethyl methacrylate, and methylmethacrylate.

Examples of other ethylenically unsaturated groups that may be used in the precursors include acrylamides and methacrylamides (such as 2-acrylamido-2-methyl-1-propanesulfonic, (3-acrylamidopropyl)trimethylammonium chloride, N-acryloylamido-ethoxyethanol, 3-Acryloylamino-1-propanol, N-tert-butylacrylamide, diacetone acrylamide, N,N-dimethylacrylamide, N-[3-(dimethylamino)propyl]methacrylamide, N-diphenylmethylacrylamide, N,N'-hexamethylenebis(methacrylamide), N-hydroxyethyl acrylamide, N-(hydroxymethyl)acrylamide, N-(isobutoxymethyl)acrylamide, N-isopropylacrylamide, N-isopropylmethacrylamide, methacrylamide, N-(3-methoxypropyl)acrylamide, N-phenylacrylamide, N-(triphenylmethyl)methacrylamide, N-[tris(hydroxymethyl)methyl]acrylamide), acid acrylates (such as acryloyl chloride, 4-acryloylmorpholine, [2-(Acryloyloxy)ethyl]trimethylammonium chloride, 2-(4-benzoyl-3-hydroxyphenoxy)ethyl acrylate, benzyl 2-propylacrylate, butyl acrylate, tert-butyl acrylate, 2-[[(butylamino)carbonyl]oxy]ethyl acrylate, tert-butyl 2-bromoacrylate, 4-tert-Butylcyclohexyl acrylate, 2-carboxyethyl acrylate, 2-chloroethyl acrylate, 2-(diethylamino)ethyl acrylate, di(ethylene glycol)ethyl ether acrylate, di(ethylene glycol) 2-ethylhexyl ether acrylate, 2-(dimethylamino)ethyl acrylate, 3-(dimethylamino)propyl acrylate, dipentaerythritol penta-/hexa-acrylate, ethyl acrylate, 2-ethylacryloyl chloride, ethyl 2-(bromomethyl)acrylate, ethyl cis-(β-cyano)acrylate, ethylene glycol dicyclopentenyl ether acrylate, ethylene glycol methyl ether acrylate, ethylene glycol phenyl ether acrylate, ethyl 2-ethylacrylate, 2-ethylhexyl acrylate, ethyl 2-propylacrylate, ethyl 2-(trimethylsilylmethyl)acrylate, hexyl acrylate, 4-hydroxybutyl acrylate, 2-hydroxyethyl acrylate, 2-hydroxy-3-phenoxypropyl acrylate, hydroxypropyl acrylate, isobornyl acrylate, isobutyl acrylate, isodecyl acrylate, isooctyl acrylate, lauryl acrylate, methyl 2-acetamidoacrylate, methyl acrylate, methyl α-bromoacrylate, methyl 2-(bromomethyl)acrylate, methyl 3-hydroxy-2-methylenebutyrate, methyl 2-(trifluoromethyl)acrylate, neopentyl glycol methyl ether propoxylate (2PO/OH) acrylate, octadecyl acrylate, pentabromobenzyl acrylate, pentabromophenyl acrylate, pentafluorophenyl acrylate, poly(ethylene glycol) methyl ether acrylate, poly(propylene glycol) acrylate, soybean oil, epoxidized acrylate, 3-sulfopropyl acrylate, tetrahydrofurfuryl acrylate, 3-(trimethoxysilyl)propyl acrylate,5,5-trimethylhexyl acrylate, 10-undecenyl acrylate), acrylic acids and salts of acrylic acid (such as acrylic acid anhydrous, 2-bromoacrylic acid, 2-(bromomethyl)acrylic acid, 2-ethylacrylic acid, hafnium carboxyethyl acrylate, methacrylic acid, 2-propylacrylic acid, sodium acrylate, sodium methacrylate, 2-(trifluoromethyl)acrylic, zinc acrylate, zirconium acrylate, zirconium bromonorbornanelactone carboxylate triacrylate, and zirconium carboxyethyl acrylate), acrylonitriles (such as acrylonitrile, 1-cyanovinyl acetate, and ethyl 2-cyanoacrylate), bisphenol acrylics (such as bisphenol A ethoxylate diacrylate, bisphenol A glycerolate dimethacrylate, bisphenol A glycerolate (1 glycerol/phenol)diacrylate, bisphenol A dimethacrylate, and bisphenol F ethoxylate (2 EO/phenol) diacrylate), fluorinated acrylics (such as 2,2,3,3,4,4,5,5,6,6,7,7-dodecafluoroheptyl acrylate, 3,3,4,4,5,5,6,6,7,7,8,8,9,9,10,10,11,12,12,12-eicosafluoro-11-(trifluoromethyl)dodecyl methacrylate, 3,3,4,4,5,5,6,6,7,7,8,8,9,9,10,10,11,11,12,12,12-Heneicosafluorododecyl acrylate, 3,3,4,4,5,5,6,6,7,7,8,8,9,9,10,10,11,11,12,12,12-Heneicosafluorododecyl methacrylate, 3,3,4,4,5,5,6,6,7,7,8,8,9,9,10,10-heptadecafluorodecyl methacrylate, 2,2,3,3,4,4,4-heptafluorobutyl acrylate, 2,2,3,3,4,4,4-heptafluorobutyl methacrylate, 2,2,3,4,4,4-hexafluorobutyl acrylate, 2,2,3,4,4,4-hexafluorobutyl methacrylate, 1,1,1,3,3,3-hexafluoroisopropyl acrylate, 1,1,1,3,3,3-hexafluoroisopropyl methacrylate, 2,2,3,3,4,4,5,5-octafluoropentyl acrylate, 2,2,3,3,4,4,5,5-octafluoropentyl methacrylate, 2,2,3,3,3-pentafluoropropyl acrylate, 2,2,3,3,3-pentafluoropropyl methacrylate, 1H,1H,2H,2H-perfluorodecyl acrylate, 2,2,3,3-tetrafluoropropyl methacrylate, 3,3,4,4,5,5,6,6,7,7,8,8,8-tridecafluorooctyl acrylate, 2,2,2-trifluoroethyl methacrylate, 1,1,1-trifluoro-2-(trifluoromethyl)-2-hydroxy-4-methyl-5-pentyl methacrylate, and 2-[(1',1',1'-trifluoro-2'-(trifluoromethyl)-2'-hydroxy)propyl]-3-norbornyl methacrylate), malemides (such as 2-[8-(3-hexyl-2,6-dioctylcyclohexyl)octyl]pyromellitic diimide oligomer, maleimide terminated, 2-[8-(3-Hexyl-2,6-dioctylcyclohexyl)octyl]pyromellitic diimide oligomer, maleimide terminated, N,N'-(o-phenylene)dimaleimide, N,N'-(1,3-phenylene)dimaleimide, and N,N'-(1,4-phenylene)dimaleimide), methacrylates (such as allyl methacrylate, 2-aminoethyl methacrylate, 2-[3-(2H-benzotriazol-2-yl)-4-hydroxyphenyl]ethyl methacrylate, benzyl methacrylate, bis(2-methacryloyl)oxyethyl disulfide,2-(2-bromoisobutyryloxy)ethyl methacrylate,2-(tert-butylamino)ethyl methacrylate, butyl methacrylate, tert-butyl methacrylate, 9H-carbazole-9-ethylmethacrylate, 3-chloro-2-hydroxypropyl methacrylate, cyclohexyl methacrylate, 2-(diethylamino)ethyl methacrylate, Di(ethylene glycol) methyl ether methacrylate, 2-(diisopropylamino)ethyl methacrylate, 2-(dimethylamino)ethyl methacrylate, 2-ethoxyethyl methacrylate, ethylene glycol dicyclopentenyl ether methacrylate, ethylene glycol methyl ether methacrylate, ethylene glycol phenyl ether methacrylate, 2-ethylhexyl methacrylate, ethyl methacrylate, ferrocenylmethyl methacrylate, furfuryl methacrylate, glycidyl methacrylate, glycidyl methacrylate, glycosyloxyethyl methacrylate, hexyl methacrylate, hydroxybutyl methacrylate, 2-hydroxyethyl methacrylate, 2-hydroxyethyl methacrylate, hydroxypropyl methacrylate, 2-hydroxypropyl 2-(methacryloyloxy)ethyl phthalate, isobornyl methacrylate, isobutyl methacrylate, 2-isocyanatoethyl methacrylate, isodecyl methacrylate, lauryl methacrylate, methacrylic acid N-hydroxysuccinimide ester, [3-(methacryloylamino)propyl]dimethyl(3-sulfopropyl)ammonium hydroxide, [3-(methacryloylamino)propyl] trimethylammonium chloride, methacryloyl chloride purum, methacryloyl chloride, [2-(methacryloyloxy)ethyl]dimethyl-(3-sulfopropyl)ammonium hydroxide, 2-methacryloyloxyethyl phosphorylcholine, [2-(methacryloyloxy)ethyl] trimethylammonium chloride, [2-(methacryloyloxy)ethyl] trimethylammonium methyl sulfate, 2-(methylthio)ethyl methacrylate, mono-2-(methacryloyloxy)ethyl maleate, mono-2-(methacryloyloxy)ethyl succinate, 2-N-morpholinoethyl methacrylate, 1-naphthyl methacrylate, pentabromophenyl methacrylate, pentafluorophenyl methacrylate, phenyl methacrylate, phosphoric acid 2-hydroxyethyl methacrylate ester, poly(ethylene glycol) behenyl ether methacrylate, poly(ethylene glycol) 2,4,6-tris(1-phenylethyl)phenyl ether methacrylate, poly(propylene glycol) methacrylate, propyl methacrylate, 1-pyrenemethyl methacrylate, solketal methacrylate, stearyl methacrylate, 3-sulfopropyl methacrylate, TEMPO methacrylate, tetrahydrofurfuryl methacrylate, 2,4,6-tribromophenyl methacrylate, 3-(trichlorosilyl)propyl methacrylate, triethylene glycol methyl ether methacrylate, 1,1,1-trifluoro-2-(trifluoromethyl)-2-hydroxy-4-methyl-5-pentyl methacrylate, 2-[(1',1', 1'-trifluoro-2'-(trifluoromethyl)-2'-hydroxy)propyl]-3-norbornyl methacrylate, 3-(trimethoxysilyl)propyl methacrylate, 3,3,5-trimethylcyclohexyl methacrylate, (trimethylsilyl)methacrylate, 2-(trimethylsilyloxy)ethyl methacrylate, 3-[tris(trimethylsiloxy)silyl]propyl methacrylate, and vinyl methacrylate), and polyfunctional acrylics (such as acrylamide: N,N'-methylenebisacrylamide, 3-(acryloyloxy)-2-hydroxypropyl methacrylate, bis[2-(methacryloyloxy)ethyl]phosphate, bisphenol A propoxylate diacrylate, 1,3-butanediol diacrylate, 1,4-butanediol, 1,3-butanediol dimethacrylate, 1,4-butanedioldimethacrylate, N,N'-(1,2-dihydroxyethylene)bisacrylamide, di(trimethylolpropane) tetraacrylate, diurethane dimethacrylate, N,N'-ethylenebis(acrylamide), glycerol 1,3-diglycerolate diacrylate, glycerol dimethacrylate, glycerol propoxylate, 1,6-hexanediol diacrylate, 1,6-hexanediol dimethacrylate, 1,6-hexanediol ethoxylate diacrylate, hydroxypivalyl hydroxypivalate, bis[6-(acryloyloxy)hexanoate], neopentyl glycol diacrylate, neopentyl glycol propoxylate, pentaerythritol diacrylate monostearate, pentaerythritol tetraacrylate, pentaerythritol triacrylate, poly(propylene glycol) diacrylate, poly(propylene glycol) dimethacrylate,1,3,5-triacryloylhexahydro-1,3, 5-triazine, tricyclo[5.2.1.02,6]decanedimethanol diacrylate, trimethylolpropane ethoxylate, trimethylolpropane ethoxylate triacrylate, trimethylolpropane ethoxylate triacrylate, trimethylolpropane ethoxylate triacrylate, trimethylolpropane propoxylate triacrylate, Trimethylolpropane triacrylate, trimethylolpropane trimethacrylate, tri(propylene glycol) diacrylate, and tris[2-(acryloyloxy)ethyl]isocyanurate and salts and variations thereof.

In some implementations, a layer is formed from a co-polymer of urethane dimethacrylate and methyl methacrylate, examples of which are disclosed in, e.g., U.S. Pat. Nos. 9,750,842 and 10,519,270 and US Patent Publication No. 2020/0087440 A1, the entire contents of which are incorporated by reference for all purposes as if fully set forth herein. The urethane dimethacrylate may comprise soft segments selected, for example, from polybutadiene, polyethylene oxide (PEO), hydroxy terminated butadiene, hydroxybutyl-terminated polydimethylsiloxane (PDMS), hydroxyl terminated polyisobutylene, poly(1,6-hexyl-1,2-ethyl carbonate), polycaprolactone, polycarbonate, polyethylene adipate, polyhexamethylene carbonate glycol, poly propylene oxide (PPO), polytetramethylene adipate, poly (dimethylsiloxane), and poly(tetramethylene oxide) (PTMO). The urethane dimethacrylate may comprise hard segments formed, for example, from 1,5-napthalene diisocyanate (NDI), 2,6-toluene diisocyanate or 2,4-toluene diisocyanate (TDI), 3,3-bitoluene diisocyanate (TODI), cyclohexyl diisocyanate (CHDI), hexamethyl diisocyanate (HDI), isophorone diisocyanate (IPDI), methylene bis(p-phenyl) isocyanate, methylene diphenylisocyanate (MDI), and methylene bis(p-cyclohexyl isocyanate (HMDI). In some implementations, the urethane dimethacrylate includes soft segments based on PTMO having one or more molecular weights (Mn) between about 100 Da and about 5000 Da (e.g., about 200 Da to about 2000 Da, about 400 Da to about 1500 Da, about 650 Da, or about 1000 Da). In some implementations, the urethane dimethacrylate includes soft segments based on a mixture of PTMO having a molecular weight of about 650 Da and PTMO having a molecular weight of about 1000 Da at a defined molar ratio, such as a molar ratio 1:5, 1:4, 1:3, 1:2, 1:1:2:1, 3:1, 4:1, or 5:1 (e.g., 1:1). The molecular weight of the PTMO may be varied to adjust the stiffness of the layer.

As described in the foregoing, a biomimetic osteochondral implant may have a base layer, such as base zone 112 of implant 100 of FIG. 1A, that interfaces with bone post-implantation (e.g., by any of the attachment mechanisms described in relation to FIGS. 8A-8I). The base layer may be porous. The base layer may be formed from any biocompatible material with the appropriate structural and/or mechanical properties. For example, the biocompatible material may be selected to have mechanical properties of the bone where the implant is anchored. The porosity of the materials may also be engineered or chosen to be advantageous for angiogenesis and bone ingrowth.

In some implementations, the base layer may be formed from a stiff, non-resorbable thermoplastic that can be caused to flow with ultrasonic welding vibration, ultrasonic energy, laser energy, heat, RF energy and electrical energy, e.g., polycarbonate urethane, polyether urethane, and PEEK.

In some implementations, the base layer is porous bone, e.g., cancellous bone from a human (an allograft) or animal (a xenograft). If a synthetic bone-like material is used, it can be formed from porous calcium-phosphate (or other materials, including but not limited to porous carbonated apatite, beta-tricalcium phosphate, or hydroxyapatite), or a porous resorbable or non-resorbable thermoplastic as described above.

In some implementations, the base layer comprises a metal, such as titanium, tantalum, stainless steel, cobalt chrome, a nickel-titanium alloy (i.e., Nitinol), or a zirconium alloy. In some implementations, the base layer is porous titanium. The base layer may be a metal having a surface coating, for example, on one or both of the outer base surface and inner base surface. The base layer may have a plasma-sprayed titanium coating or a plasma-sprayed ceramic coating on one or both surfaces.

In some embodiments, the base layer is a ceramic, e.g., a resorbable ceramic or a non-resorbable ceramic.

In some embodiments, the base layer may include an additional material depending on the intended anatomic application. For example, if an implant is used to repair a defect in the glenoid in the scapula which has very thin cancellous and cortical bone, a bone growth inducing or enticing material may be infused into the base layer. The base layer may also be combined with mechanical fastening means such as screws, pins, anchors, and stems (including any of the attachment mechanisms shown/described in FIGS. 8A-8I, and it may be formed from non-resorbable materials or resorbable materials engineered to be replaced by natural tissues over time.

As described above, a bonding agent (e.g., a polymeric adhesive, a bone cement such as PMMA, an epoxy, a glue, or a grout) is applied between a first layer 802 (e.g., the inner base surface 115 of implant 100, the outer base surface 208 or inner base surface 209 of two-layered implant 200, or the inner base surface 315 of three-layered construct 300) and a second layer 806 (e.g., bone, or under surface 205 of implant 200).

In some implementations, the bonding agent is a polymeric adhesive that comprises a first precursor and a second precursor as discussed above. In some implementations, the bonding agent is a polymeric adhesive that comprises urethane dimethacrylate and methyl methacrylate. After application, the polymeric adhesive may be cured using radiation, such as visible light, infrared light, or ultraviolet light using a photoinitiator; or cured using a thermal initiator (e.g., benzoyl peroxide), chemical initiator or catalysts, and/or redox activated initiation systems, for example, one comprising camphorquinone. A combination of photo-initiation and non-light-based initiation systems such as thermal, chemical, and/or redox systems may be used. An accelerating agent, such as N,N-dimethyl-p-toluidine, may also be used.

The urethane dimethacrylate may comprise soft segments selected, for example, from polybutadiene, polyethylene oxide (PEO), hydroxy terminated butadiene, hydroxybutyl-terminated polydimethylsiloxane (PDMS), hydroxyl terminated polyisobutylene, poly(1,6-hexyl-1,2-ethyl carbonate), polycaprolactone, polycarbonate, polyethylene adipate, polyhexamethylene carbonate glycol, polypropylene oxide (PPO), polytetramethylene adipate, poly(dimethylsiloxane), and poly(tetramethylene oxide) (PTMO). The urethane dimethacrylate may comprise hard segments formed, for example, from 1,5-napthalene diisocyanate (NDI), toluene-2,6-diisocyanate or toluene-2,4-diisocyanate (TDI), 3,3'-bitoluene diisocyanate (TODI), cyclohexyl diisocyanate (CHDI), hexamethyl diisocyanate (HDI), isophorone diisocyanate (IPDI), methylene bis(p-phenyl) isocyanate, methylene diphenylisocyanate (MDI), and methylene bis(p-cyclohexyl isocyanate (HMDI). In some implementations, the urethane dimethacrylate includes soft segments based on PTMO having one or more molecular weights between about 100 Da and about 5000 Da (e.g., about 250 Da to about 2500 Da, about 400 Da to about 2000 Da, about 500 Da to about 1250 Da, about 250 Da, about 400 Da, about 500 Da, about 650 Da, about 800 Da, about 1000 Da, about 1250 Da, about 1500 Da about 2000 Da, about 2500 Da, about 4000 Da, about 5000 Da, or a mixture thereof). In some implementations, the urethane dimethacrylate includes soft segments based on a mixture of two or more (e.g., two, three, or four) PTMO each having molecular weights of about 500 Da to about 1250 Da at any molar ratio (e.g., a mixture of PTMO having a molecular weight of 650 Pa and 1000 Pa at a defined molar ratio, such as a molar ratio 1:5, 1:4, 1:3, 1:2, 1:1:2:1, 3:1, 4:1, or 5:1 (e.g., 1:1)). The molecular weight(s) of the PTMO may be varied to adjust the stiffness of the polymeric adhesive after it is cured.

In some implementations, the urethane dimethacrylate comprises about 60% (w/w) to about 80% (w/w), about 60% (w/w) to about 90% (w/w), about 60% (w/w) to about 99% (w/w), or about 70% (w/w) to about 90% (w/w) of the polymeric adhesive. In some implementations, the methyl methacrylate regions comprise about 20% (w/w) to about 40% (w/w), about 1% to about 20% (w/w), or about 1% (w/w) to about 40% (w/w), or about 25% (w/w) to about 35% (w/w) of the polymeric adhesive. In some implementations, the polymeric adhesive is formed from urethane dimethacrylate and methyl methacrylate and defines a tensile modulus between about 30 MPa and about 2000 MPa (e.g., about 100 MPa to about 1000 MPa, about 200 MPa to about 500 MPa, about 200 MPa, about 300 MPa, about 400 MPa, or about 500 MPa). In some implementations, the polymeric adhesive is formed from urethane dimethacrylate and methyl methacrylate and defines a failure strain between about 25% and 200%. In some implementations, the polymeric adhesive is formed from urethane dimethacrylate and methyl methacrylate and defines a compressive modulus between about 30 MPa and about 2000 MPa (e.g., about 30 MPa to about 500 MPa, about 50 MPa to about 250 MPa, about 100 MPa to about 200 MPa, or about 75 MPa, about 100 MPa, about 120 MPa, about 150 MPa, about 180 MPa, or about 200 MPa).

Exemplary polymeric adhesives and methods of preparing the same are disclosed in, e.g., U.S. Pat. Nos. 9,750,842 and 10,519,270 and US Patent Publication No. 2020/0087440 A1, the entire contents of which are incorporated by reference for all purposes as if fully set forth herein.

Example 1: Finite Element Analysis (FEA) Contact Pressure Assessment of the Native Knee and Various Round Implant Designs A study was conducted to create a knee model to assess the contact pressure between the femur and tibia with a three-layered implant. The sample consisted of the following materials: 1) a first layer of a semi-interpenetrating polymeric network that includes polyurethane and polyacrylic acid that is sulfonated, 2) a second layer of UDMA-MMA copolymer and 3) a third layer of the porous titanium (an example of a three-layer implant). The top layer is a semi-interpenetrating polymeric network that includes polyurethane and polyacrylic acid that is sulfonated, the middle layer is formed from a UDMA-MMA copolymer, and the bottom layer is porous titanium. The three-layered implant was also compared against a CoCr implant with the same geometry as the two polymeric layers attached to the same porous material. A range of implant diameters (12-24 mm) and articular surface curvatures were examined that were appropriately sized to the femoral condyles.

A knee model was constructed from imaging data derived from a healthy patient. The model included the femur, tibia, and meniscus. The femur and tibial models both included the articular cartilage. The joint was oriented at a 15° flexion angle and a load of 3100 N (~3 MPa average pressure) was applied across the joint. This flexion angle and load magnitude are representative of that observed during walking.

The contact pressures were acquired for the native joint. A cylindrical defect was then created in the medial condyle of the femur in the center of pressure observed in the native intact knee. The three-layered implant was then inserted into the defect and the contact pressure measurement repeated. Finally, the CoCr implant was inserted into the defect and the contact pressure measurement repeated.

In all implant cases, the implant was seated into the defect to ensure that the edge of the implant was below the adjacent cartilage, and the center of the implant was proud (as illustrated in FIG. 4A), even or below the original cartilage surface In a series of simulations on peak contact pressures for a variety of conditions and implants, the three-layer implant consistently exhibited lower peak contact pressures than the native knee while the CoCr implant consistently exhibited higher than native peak contact pressures. The pressures are charted in FIG. 10 to demonstrate the differences in peak contact pressure between the various implants and situations examined. The chart shows the range of observed values for the three-layer and CoCr implants. The results, indicated that the three-layered implant successfully reduced the peak contact pressure in the knee without a direct match of the articular surface. In a direct comparison to CoCr, the contact pressures for the three-layered implant were observed in a range between 3.4 and 5.8 MPa which was found to be less than that observed for the CoCr implant (5.0 to 10.5 MPa) in comparable settings (geometry and seating conditions).

Example 2: Creep and Relaxation Assessment of 1st Polymer, 2nd Polymer and 3 Layer Implant A study was conducted to assess the confined creep and relaxation of sample implants, which are examples of the biomimetic osteochondral implants described herein, under physiological loads. Three samples were tested: 1) An 8 mm diameter piece of semi-interpenetrating polymeric network that includes polyurethane and polyacrylic acid that is sulfonated, 2) an 8 mm diameter piece of UDMA-MMA copolymer and 3) an 8 mm diameter construct with a semi-IPN layer, a UDMA-MMA copolymer layer, and a porous titanium layer (an example of a three-layer implant).

Figure 11:
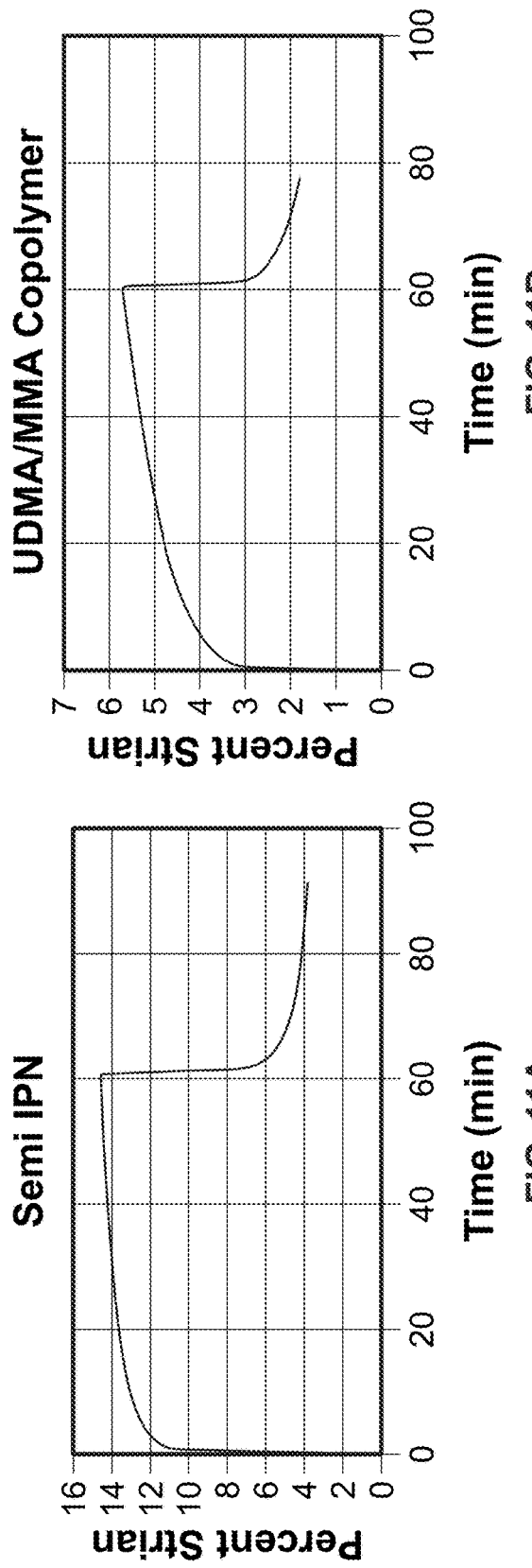
FIG. 11A is a plot of the creep and relaxation behavior of a semi-IPN polymer.
FIG. 11B is a plot of the creep and relaxation behavior of a UDMA-MMA copolymer.
FIG. 11C is a plot of the creep and relaxation behavior of a construct of a semi-IPN polymer layer, a UDMA-MMA copolymer layer and a porous titanium layer.

A load of 3 MPa was applied to each material for 1 hour in confined creep and then allowed to relax for 30 minutes. The semi-IPN yielded creep of 10-20% and recovery of 50-100%. The UDMA-MMA copolymer yielded creep of 2-10% and recovery of 60-90%. The construct yielded creep of 5-7% and recover of 90-100%. Representative curves from this testing can be found in FIGS. 11A, 11B, and 11C.

Implantation Methods

Also provided herein are methods of implanting the biomimetic osteochondral implants discussed herein. Any of the implants shown in and described in relation to FIGS. 1A-9J may be implanted according to these methods.

In some implementations, a biomimetic osteochondral implant is used to repair an osteochondral defect in a joint. After obtaining access to the osteochondral lesion through an appropriate approach for the given joint a sizing device is used to aide in the selection of an implant that will cover the lesion and result in a stable cartilage margin. Then, a wire (e.g., k-wire) or a pin (e.g., Steinmann pin) is placed into the center of the lesion with the use of a guide that approximates the size of the implant. The guide ensures that the wire is placed perpendicular to the joint surface. This guide may have a geometry that conforms to the articular surface of the joint being treated. After insertion of the wire or pin, the guide is removed from the surgical site.

An incising or cutting tool may be used to incise the cartilage to create a clean margin. The incisor is placed over the previously placed guide wire to ensure proper alignment. A drill, burr or reamer is then used to create a cavity in the bone that is designed to receive the implant (i.e., an implantation site). The drill, burr, or reamer is placed over the wire or pin to ensure proper alignment. This cavity may create a press-fit with the implant to provide initial fixation. This cavity may also be designed to receive posts, threads, or other means of securing the implant into the prepared cavity. The cavity may also be created in order to gain access to cancellous bone for adhesive penetration and attachment when the second polymer layer is adhered to the bone in vivo via a bonding agent. The drill may be used with a separate guide, possess markings or have a shoulder to ensure that the cavity is drilled to the appropriate depth. After the cavity has been created, the wire or pin is removed.

The cavity is then verified for accuracy and fit with the use of a trial. The trial mimics the geometry of the implant and allows assessment of the desired seating depth and placement of the implant. After the assessment is complete, the trial is removed from the cavity. If required, the wire or pin can be reinserted and the drill used again to adjust the depth of the cavity if the implant seating was not sufficiently deep. The implant will then be placed into the cavity. The exact insertion technique will depend on the chosen implant geometry (e.g., press fit, post(s), thread, etc.).

In some implementations, the implant is seated with the edge of the implant recessed below the surrounding cartilage where the center of the implant may be proud of the original joint line (FIG. 4A). After the implant is loaded, the conformity of the implant will improve in vivo to match the surrounding cartilage due to a combination of elastic deformation and time dependent creep of the bearing zone (FIG. 4B).

Figure 12:
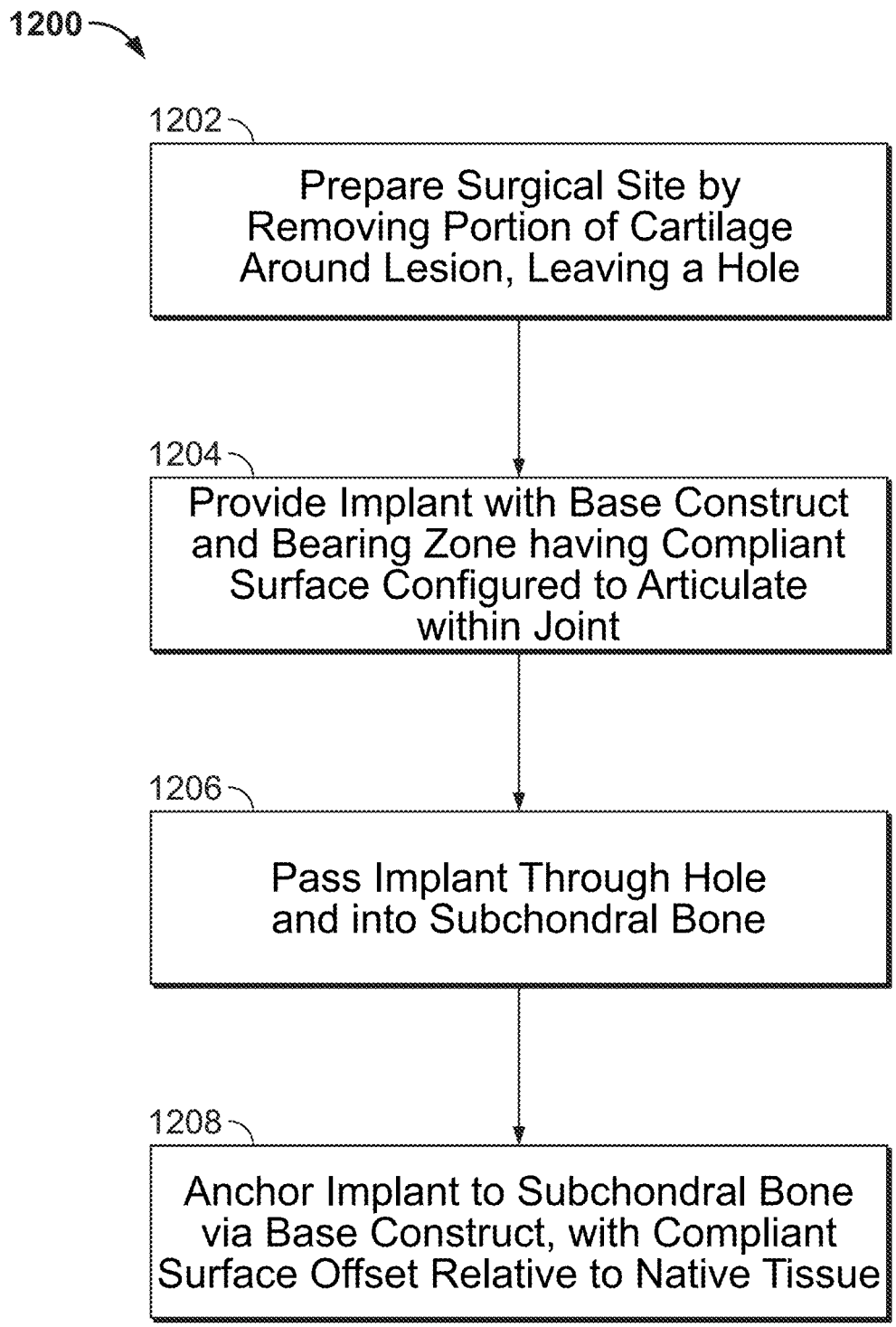
FIG. 12 shows a flowchart for a method of repairing a cartilage lesion on an articulating surface within an orthopedic joint, according to an illustrative implementation.

FIG. 12 is a flowchart describing a method 1200 for repairing a cartilage lesion on an articulating surface within a joint (e.g., a diarthrodial joint). The joint comprises bone, and the lesion is at least partially surrounded by exterior cartilage on the articulating surface, a portion of the exterior cartilage providing a region with a native tissue line for articulation. Method 1200 comprises steps 1202, 1204, 1206, and 1208. Step 1202 comprises preparing a surgical site in the exterior cartilage region by removing at least a portion of the cartilage surrounding the lesion and leaving a hole that extends through the exterior cartilage region and into the bone. The hole in the exterior cartilage has an inside diameter. Step 1204 comprises providing a biomimetic osteochondral implant comprising a bearing zone and a base construct. The implant may be any of the implants described herein, such as the implants shown in and described in relation to FIGS. 1A-9J. The bearing zone has an under surface and a compliant surface with an outer face and a first perimeter having an outside diameter, the compliant surface configured to change shape upon articulation within the diarthrodial joint so the outer face conforms in shape to an opposing surface of the orthopedic joint. Step 1206 comprises passing the implant through the hole and into bone so that the base construct interfaces directly with the bone. Step 1208 comprises anchoring the implant to the bone so that the outer face of the compliant surface is offset in height relative to the native tissue line of the exterior cartilage.

The bearing zone may have a first stiffness, and the base construct may have a second stiffness greater than the first stiffness. The bearing zone may have a stiffness gradient extending from the compliant surface to the under surface. For example, the stiffness at the compliant surface may be less than the stiffness at the under surface. As described above, the bearing zone may comprise a biphasic polymer with a water composition gradient, as described in the foregoing. The bearing zone may comprise urethane. The bearing zone may be lubricious or non-lubricious at the surfaces. The base construct may comprise a metal, ceramic, bone, synthetic bone, or polymer.

In some implementations, the bearing zone is a first polymeric layer disposed between the compliant surface and the under surface, and the base construct comprises a porous layer configured to attach directly to the bone and second polymeric layer attached to the first polymeric layer at a middle interface between the under surface and a shaped surface of the second polymeric layer, such that the second layer is disposed between the middle interface and the porous layer. The first polymeric layer has a first stiffness and the second polymeric layer has a second stiffness, and wherein the second stiffness is greater than the first stiffness. The first polymeric layer may have a first stiffness and the second polymeric layer has a second stiffness, and wherein the second stiffness is greater than the first stiffness. Additionally, the porous layer may have a third stiffness greater than the second stiffness.

In some implementations, the first polymeric layer is a water-swellable interpenetrating polymer network (IPN) or semi-IPN that comprises a first polymeric network comprising the thermoplastic polymer and a second polymeric network. In some implementations, the second polymeric layer comprises a copolymer of urethane dimethacrylate monomer comprising a hard segment and a soft segment, and methyl methacrylate monomer. The hard segment of the urethane dimethacrylate of the first polymeric adhesive may be formed from one or more of 1,5-naphthalene diisocyanate (NDI), 2,6 toluene diisocyanate or 2,4 toluene diisocyanate (TDI), 3,3-bitoluene diisocyanate (TODI), cyclohexyl diisocyanate (CHDI), hexamethyl diisocyanate (HDI), isophorone diisocyanate (IPDI), methylene bis(p-phenyl) isocyanate, methylene diphenylisocyanate (MDI), and methylene bis(p-cyclohexyl) isocyanate (HMDI). The soft segment of the urethane dimethacrylate monomer may be formed from one or more of polybutadiene, polyethylene oxide (PEO), hydroxy terminated butadiene, hydroxybutyl-terminated polydimethylsiloxane (PDMS), hydroxyl terminated polyisobutylene, poly(1,6-hexyl-1,2-ethyl carbonate), polycaprolactone, polycarbonate, polyethylene adipate, polyhexamethylene carbonate glycol, polypropylene oxide (PPO), polytetramethylene adipate, poly(dimethylsiloxane), and poly(tetramethylene oxide) (PTMO).

The implant may be planar, plano-convex or plano-concave, or any combination thereof. The bearing zone may be aligned laterally along the first perimeter with the surrounding exterior cartilage, such that the bearing cartilage is in contact with the exterior cartilage along the first perimeter. Sides of the implant may be completely in contact with the surrounding cartilage defining the hole such that the implant is press-fit into the hole when implanted and anchored. The compliant surface may be offset from the native tissue line in a direction distal to the bone or in a direction proximal to the bone. The bearing zone may vary in thickness, such that the edge of the compliant surface is offset from the native tissue line is one direction and the center of the compliant surface if offset from the native tissue line in an opposite direction.

Method 1200 may be used for osteochondral defect repair at various physiological sites, including but not limited to articulating surfaces in diarthrodial joints. Suitable sites include a knee joint (e.g., a condyle, a patellofemoral joint, a total knee joint, a meniscus, a patella, or a tibial plateau), an ankle joint (e.g., talar or tibial surfaces), an elbow joint (e.g., proximal ulna, distal humerus, or radial head), a shoulder joint (e.g., a labrum, a glenoid, a humeral head or any portion thereof), a hand joint (e.g., a metacarpal joint, a finger joint, a thumb joint, or a base of thumb joint), a hip joint (e.g., the acetabular surface, a femoral head or a portion of either surface), a foot joint (e.g., a metatarsal joint or a toe joint), a jaw joint (e.g., a temporomandibular joint), a wrist joint, a vertebral joint (e.g., an intervertebral facet joint), and any portion thereof. Method 1200 is not limited to use in humans and can be used for osteochondral repair in other organisms, particularly those having orthopedic joints or articulating cartilage.

In some implementations, step 1202 comprises using at least one of an awl, a surgical drill, a burr, a reamer, an alignment guide, a pin, an incisor, a cutter, or a wire. Any of these tools may be used to prepare a surgical site or remove cartilage. Step 1202 may involve inserting a wire or a pin into the lesion via a guide, placing a drill, burr, or reamer over the wire or pin, and forming the hole using the drill, burr, or reamer. In some implementations, step 1202 comprises resurfacing of bone within the hole.

In some implementations, prior to step 1206, method 1200 further comprises checking a depth of the hole. Checking the depth may involve inserting a trial implant into the hole, where the trial implant mimics the size and shape of the implant.

Step 1206 may involve using an implant inserting device, such as a clamp or threaded rod, which releasably holds the implant. Step 1208 may involve using a mallet and a tamp to fully seat the implant within the hole. Step 1208 may involve the use of any attachment mechanism 822 of FIGS. 8A-8I. Step 1208 may comprise allowing the bone to grow new bone into the base construct. For example, step 1208 spans a time period, where at the beginning of the time period the base construct and the bone are physically interfaced, and at the end of the time period new bone has grown into the base construct from the bone. Method 1200 may further comprise closing the surgical site. In some implementations, one or more of steps 1202-1208 is performed through an arthroscope.

Figure 13A:
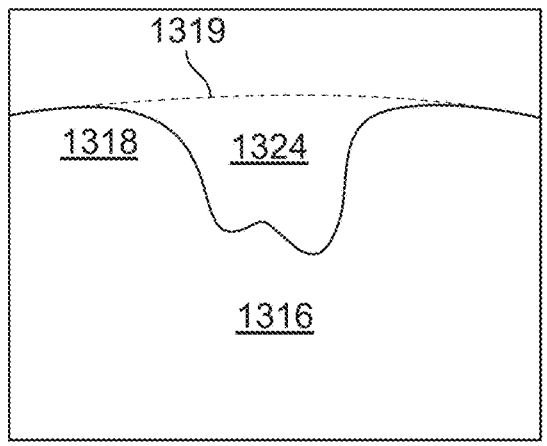
FIGS. 13A-13D depict the method of repairing a cartilage lesion on an articulating surface within an orthopedic joint, according to an illustrative implementation.

FIGS. 13A-13D illustrate an example of implantation method 1200 of FIG. 12 using a three-layered implant 1300. FIG. 13A shows the lesion 1324 disposed in native tissue 1318 and above bone 1316. The native tissue 1318 has a native tissue surface line 1319, represented by a dashed line, where the native tissue is articulated with an opposing joint surface prior to formation of the lesion.

Figure 13B:
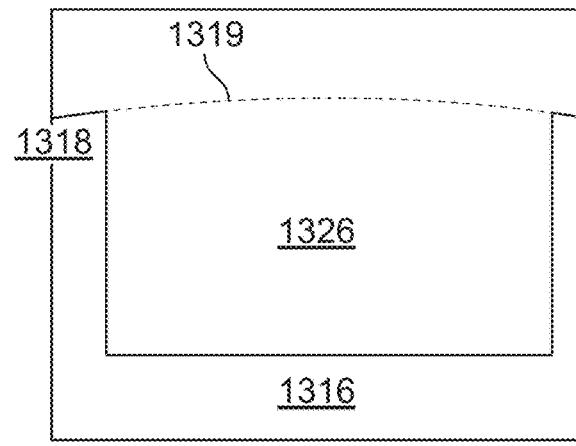

FIG. 13B shows the hole 1326 formed during step 1202 of method 1200. Hole 1326 extends from native tissue surface line 1319 to bone 1316 and is surrounded by native tissue 1318. Hole 1326 is sized and shaped so as to fit implant 1300, which may be any of the three-layered implants disclosed generally or provided specifically herein (e.g., implant 100, implant 300, implant 400, implant 500).

Figure 13C:
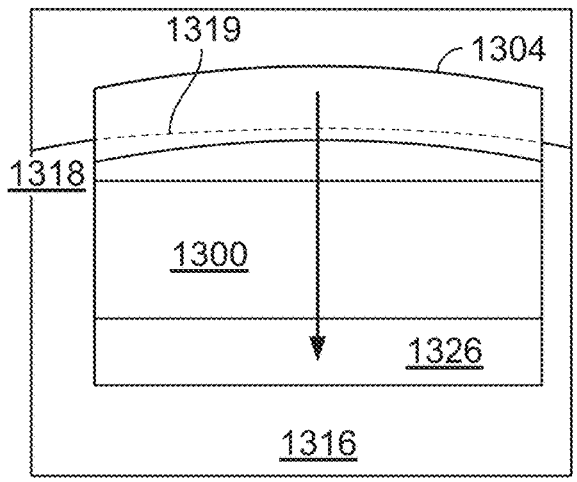

FIG. 13C shows insertion of implant 1300 during step 1206 of method 1200. Implant 1300 comprises a compliant surface 1304, a bearing zone, a middle zone, and a base zone. Implant 1300 is passed through hole 1326 and into bone 1316 so that the base zone interfaces directly with bone 1316.

Figure 13D:
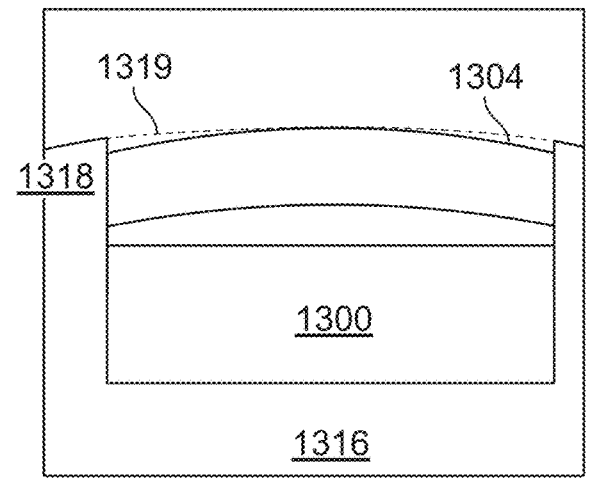

FIG. 13D shows implant 1300 fully anchored into the bone 1316. Compliant surface 1304 is offset in height relative to the native tissue surface line 1319 of the surrounding native cartilage 1318. As discussed in the foregoing, the center of compliant surface 1304 may protrude above the native tissue surface line 1319 so that, upon physiological loading, compliant surface 1304 conforms to the opposing joint surface via compression and mimics the native tissue surface line 1319.

Example 3: Implant Curvature Conformity

Figure 14C:
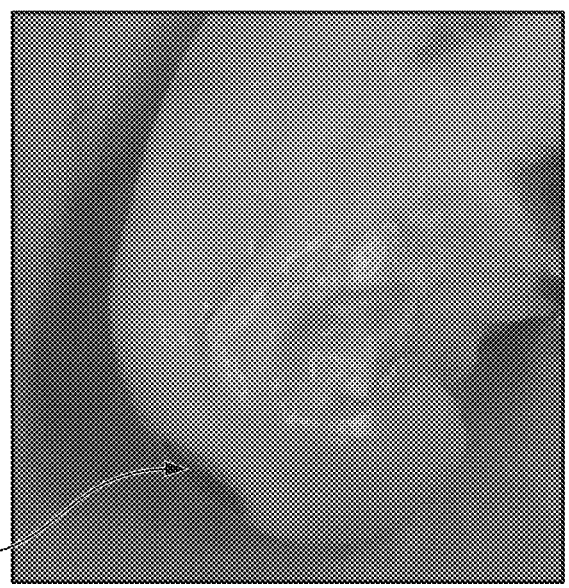
FIG. 14C is a photograph of the explant, which shows overall implant conformity to the surrounding tissue.
Figure 14B:
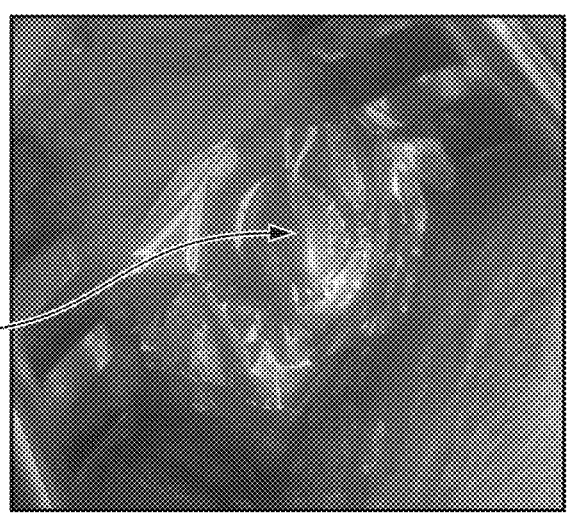
FIG. 14B is a photograph of the biomimetic osteochondral implant of FIG. 14A, in which an aluminum foil is pressed over the implant surface intraoperatively to show the surface contours of the implantation site.
Figure 14A:
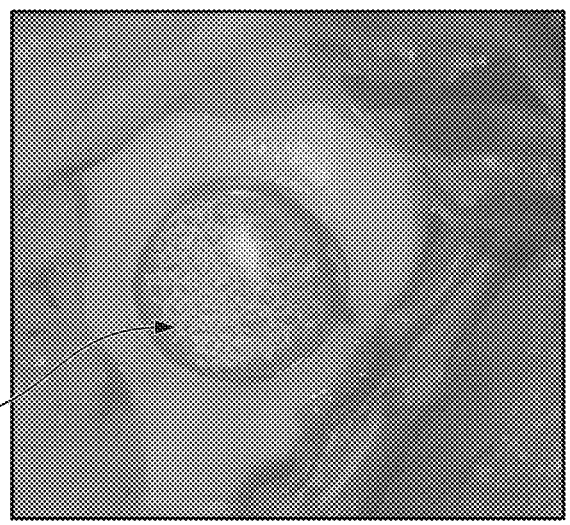
FIG. 14A is a photograph of an biomimetic osteochondral implant seated in a goat medial femoral condyle.

An 8 mm diameter version of the implant described in Example 1 was implanted in the medial femoral condyle of skeletally-mature Boer cross goats. Using a para-patellar approach, an osteochondral defect was created using a surgical drill and a depth guide. The implant was press fit in the defect and the incision was closed. Unrestricted weight-bearing and activity were allowed. Joints were explanted at 8 weeks. FIGS. 14A-14B illustrate the appearance of the implant at time of implantation with the edges of the implant recessed with respect to the surrounding cartilage. This is better visualized in FIG. 14B where a thin foil was used to create an impression to see the initial seating condition of the implant. FIG. 14C illustrates the appearance of the implant after 8 weeks, where it was found to be fully aligned with the surrounding cartilage.

Size and Shapes of Example Embodiments

As indicated above, the methods and implants are adaptable to be used in the partial or total repair of various anatomic joints. Construction of suitable implants, according to the disclosure hereof, would take into account various design parameters to provide the proper shape and size (in addition to the appropriate gradients disclosed herein) for the desire anatomic position. Table 1 illustrates examples of configurations that may be used:

TABLE 1

Example implant configurations

| Anatomy | Geometry | Min Diameter/ Width (mm) | Max Diameter/ Width (mm) | Min Length (mm) | Max Length (mm) | Min Area (cm2) | Max Area (cm2) | Area |
| --- | --- | --- | --- | --- | --- | --- | --- | --- |
| Femoral Condyles | Circular | 8 | 30 | NA | NA | 0.5 | 7.1 | circular |
| | Oval/ Racetrack | 10 | 30 | 20 | 50 | 2.0 | 15.0 | rectangular |
| | Uni- condylar | 10 | 30 | 45 | 60 | 4.5 | 18.0 | rectangular |
| Patella | Circular | 10 | 45 | NA | NA | 0.8 | 15.9 | circular |
| Trochlea | Oval/ Racetrack | 20 | 30 | 30 | 50 | 6.0 | 15.0 | rectangular |
| Hip | Hemi- spherical | 30 | 60 | NA | NA | 56.5 | 226.2 | hemispherical |

The foregoing is merely illustrative of the principles of the disclosure, and the apparatuses can be practiced by other than the described embodiments, which are presented for purposes of illustration and not of limitation. It is to be understood that the objects and methods disclosed herein, while shown for repair of cartilage lesions, may be applied to other forms of osteochondral, subchondral, or other bone repair.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

What is claimed is:

1. A biomimetic osteochondral implant comprising:
a bearing layer, a base layer configured to be attached to bone upon implantation of the implant, and a hydrophobic middle layer positioned between the bearing layer and the base layer; and wherein
the bearing layer comprises a biphasic polymer, a lubricious compliant surface configured for articulation within an orthopedic joint, a non-lubricious under surface having a composition comprising less than 10% water and adapted to provide a connection to the hydrophobic middle layer, a first thickness extending between the lubricious compliant surface and the non-lubricious under surface, and a first compressive modulus with a first stiffness;
the hydrophobic middle layer has a shaped first surface, a second surface, and a second thickness extending therebetween, the shaped first surface comprising a perimeter and an external face spaced within the perimeter and attached to the non-lubricious under surface of the bearing layer and forming an essentially hydrophobic contact interface with the non-lubricious under surface of the bearing layer, wherein the non-lubricious under surface of the bearing layer conforms in shape to the external face, and the hydrophobic middle layer further has a second compressive modulus with a second stiffness, the second stiffness being greater than the first stiffness; and
the base layer comprising a metal and having an outer base surface attached to the second surface of the hydrophobic middle layer, an inner base surface configured to attach to the bone, and a third thickness extending between the inner base surface and outer base surface, and having a third compressive modulus with a third stiffness, the third stiffness being greater than the second stiffness.

2. The implant of claim 1, wherein the bearing layer comprising the biphasic polymer has a water composition of at least 10% at the lubricious compliant surface.

3. The implant of claim 1, wherein the bearing layer comprising the biphasic polymer has a water composition gradient extending between the lubricious compliant surface and the non-lubricious under surface, the gradient comprising a first water composition at the lubricious compliant surface, a second water composition at the non-lubricious under surface, and a third water composition within a bulk of the bearing layer extending between the lubricious compliant surface and the non-lubricious under surface.

4. The implant of claim 3, wherein the first water composition at the lubricious compliant surface is greater than the third water composition, and the third water composition is greater than the second water composition at the non-lubricious under surface.

5. The implant of claim 3, wherein the bulk of the bearing layer has a bulk water composition gradient of 20 to 45%, the first water composition at the lubricious compliant surface is 40-45%, and the second water composition at the non-lubricious under surface is less than 1%.

6. The implant of claim 1, wherein the bearing layer comprises urethane.

7. The implant of claim 1, wherein the essentially hydrophobic contact interface formed between the external face and the non-lubricious under surface extends across at least 50% of the external face, at least 75% of the external face, or at least 95% of the external face.

8. The implant of claim 1, further comprising at least one post structure in the hydrophobic middle layer, wherein the at least one post structure comprises a plurality of posts in the hydrophobic middle layer.

9. The implant of claim 8, wherein the at least one post structure is positioned at the shaped first surface or at the second surface.

10. The implant of claim 1, further comprising a central axis extending through the bearing layer, the hydrophobic middle layer, and the base layer, each having an axis and being aligned coaxially along the central axis, wherein the second thickness is variable with a first height extending between the second surface and the first surface at a first position along the first surface, and a second height extending between the second surface and the first surface at a second position along the first surface.

11. The implant of claim 10, wherein the first height has a maximum at a position along the perimeter and the second height has a maximum at a position within the external face.

12. The implant of claim 11, wherein the second height is aligned co-axially with the axis of the base layer.

13. The implant of claim 11, wherein one or more of the bearing layer or the hydrophobic middle layer is convex, concave, plano-convex or plano-concave.

14. The implant of claim 13, further comprising a tapered region extending along the external face from the maximum second height toward the perimeter, such that:
the first height maximum is higher than the second height maximum, and the tapered region forms a concave curve; or
the first height maximum is lower than the second height maximum, and the tapered region forms a convex curve.

15. The implant of claim 10, wherein the perimeter includes a curved edge extending circumferentially about the central axis.

16. The implant of claim 10, further comprising a ridge region comprising at least one ridge extending radially across the external face and protruding into the non-lubricious under surface.

17. The implant of claim 10, wherein the external face includes multiple regions with differing respective radii of curvature.

18. The implant of claim 10, wherein the second thickness at a position along the perimeter has a boundary height of 0.01 mm to 10 mm or 0.2 mm to 5 mm.

19. The implant of claim 18, wherein the bearing layer and the hydrophobic middle layer extend axially from the outer base surface to the lubricious compliant surface over an axial length of 2 mm to 10 mm or 4 mm to 4.5 mm.

20. The implant of claim 1, wherein the perimeter encompasses an area having a width of 5 mm to 15 mm.

21. The implant of claim 1, wherein the second stiffness is 50 MPa to 500 MPa, wherein the first stiffness is 40 MPa to 150 MPa, and wherein the third stiffness is 1.5 GPa to 11 GPa.

22. The implant of claim 1, wherein the bearing layer has a stiffness gradient extending from the non-lubricious under surface to the lubricious compliant surface of greater than or equal to 1 kPa/mm.

23. The implant of claim 1, wherein the base layer comprises at least one of a polymer, a ceramic, bone, or synthetic bone; wherein the metal comprises one or more of titanium, tantalum, stainless steel, cobalt chrome, a nickel-titanium alloy, a zirconium alloy, a metal coated with plasma-sprayed titanium, a metal coated with a plasma-sprayed ceramic; and wherein the polymer comprises one or more of polyetheretherketone, polyethylene, polysulfone, or polypropylene.

24. The implant of claim 1, wherein the inner base surface is configured to be attached to a distal femur, a proximal tibia, a patella, a condyle, a distal tibia, a distal fibula, a calcaneus, a talus, a tibiofibular joint, a proximal humerus, a labrum, a humeral head, a glenoid, a proximal femur, a pelvis, a distal humerus, a proximal ulna, a proximal radius, a distal radius, a distal ulna, a carpal, a distal metacarpal, a proximal phalanx, a metatarsal, a temporomandibular region, or a vertebra.

25. The implant of claim 1, wherein the first thickness is 1 mm to 5 mm.

26. The implant of claim 1, wherein the bearing layer includes a water-swellable interpenetrating polymer network (IPN) or semi-IPN, the base layer includes a porous metal, and the hydrophobic middle layer includes a copolymer comprising a urethane dimethacrylate monomer and a monomer selected from methyl methacrylate, acrylamide, and dimethylacrylamide.

27. The implant of claim 1, wherein the bearing layer has the ability to deform between 2% to 25% under physiological load with repeatable recovery of greater than or equal to 70% of the deformation when said load is removed, and wherein the hydrophobic middle layer is configured to deform between 2% to 10% under physiologic load, with repeatable recovery of greater than or equal to 70% of the deformation when the physiological load is removed.

28. The implant of claim 1, wherein the implant has the ability to deform between 5% to 20% under physiological load, with repeatable recovery of greater than or equal to 80% or greater than or equal to 95%.

29. The implant of claim 1, further comprising a bonding layer extending across at least 25% of the essentially hydrophobic contact interface.

30. The implant of claim 29, wherein the bonding layer comprises covalent bonds.

* * * * *